(12) United States Patent
Bonnette et al.

(10) Patent No.: US 6,942,678 B2
(45) Date of Patent: *Sep. 13, 2005

(54) GAS INFLATION/EVACUATION SYSTEM AND SEALING SYSTEM FOR GUIDEWIRE ASSEMBLY HAVING OCCLUSIVE DEVICE

(75) Inventors: Michael J. Bonnette, Minneapolis, MN (US); Eric J. Thor, Arden Hills, MN (US); Mark L. Jenson, Greenfield, MN (US)

(73) Assignee: Possis Medical, Inc., Minneapolis, MN (US)

( * ) Notice: Subject to any disclaimer, the term of this patent is extended or adjusted under 35 U.S.C. 154(b) by 301 days.

This patent is subject to a terminal disclaimer.

(21) Appl. No.: 10/007,788

(22) Filed: Nov. 6, 2001

(65) Prior Publication Data

US 2003/0088194 A1 May 8, 2003

(51) Int. Cl.[7] .............................................. A61M 25/10
(52) U.S. Cl. ..................... 606/191; 606/192; 606/194; 604/96.01; 604/99.01
(58) Field of Search ................................. 606/191–200, 606/108, 159; 604/96.01–103, 167.01, 167.02; 600/585

(56) References Cited

U.S. PATENT DOCUMENTS

| | | | |
|---|---|---|---|
| 3,773,290 A | * | 11/1973 | Mowery ........................ 251/9 |
| 4,573,470 A | | 3/1986 | Samson et al. |
| 4,573,966 A | | 3/1986 | Weikl et al. |
| 4,636,195 A | | 1/1987 | Wolinsky |
| 4,646,719 A | | 3/1987 | Neuman et al. |
| 4,733,652 A | | 3/1988 | Kantrowitz et al. |
| 4,838,268 A | | 6/1989 | Keith et al. |
| 4,865,587 A | | 9/1989 | Walling |
| 5,059,176 A | | 10/1991 | Winters |
| 5,059,178 A | | 10/1991 | Ya |
| 5,135,482 A | | 8/1992 | Neracher |
| 5,167,239 A | | 12/1992 | Cohen et al. |
| 5,171,221 A | | 12/1992 | Samson |
| 5,195,955 A | | 3/1993 | Don Michael |
| 5,209,727 A | | 5/1993 | Radisch, Jr. et al. |
| 5,320,604 A | | 6/1994 | Walker et al. |
| 5,380,284 A | | 1/1995 | Don Michael |
| 5,514,109 A | * | 5/1996 | Mollenauer et al. ........ 604/249 |
| 5,520,645 A | | 5/1996 | Imran et al. |
| 5,688,234 A | | 11/1997 | Frisbie |
| 5,713,917 A | | 2/1998 | Leonhardt et al. |
| 5,775,327 A | | 7/1998 | Randolph et al. |
| 5,776,100 A | | 7/1998 | Forman |
| 5,779,688 A | | 7/1998 | Imran et al. |
| 5,792,179 A | | 8/1998 | Sideris |
| 5,807,330 A | | 9/1998 | Teitelbaum |
| 5,827,324 A | | 10/1998 | Cassell et al. |

(Continued)

Primary Examiner—Julian W. Woo
Assistant Examiner—Sarah Webb
(74) Attorney, Agent, or Firm—Hugh D. Jaeger, Esq.

(57) ABSTRACT

A gas inflation/evacuation system and sealing system for use with occlusive devices such as occlusive balloons in vascular procedures. The gas inflation/evacuation system is removably connectible to a proximal portion of a guidewire assembly and includes an evacuation system to evacuate the guidewire assembly and an inflation system for introducing a biocompatible gas under pressure into the guidewire assembly to inflate an occlusive device a plurality of times. A sealing system is also removably connectible to the proximal portion of the guidewire assembly and selectively seals an extended sealable section at the proximal portion of the guidewire assembly at one of a plurality of separate locations to form an airtight seal of the guidewire assembly. Each time a deflation of the occlusive device is desired in order to reestablish blood flow to the vessel downstream of the occlusive device, the extended sealable section at the proximal portion of the guidewire assembly preferably is cut distal to the location of the last seal to quickly deflate the occlusive device.

27 Claims, 14 Drawing Sheets

U.S. PATENT DOCUMENTS

| | | |
|---|---|---|
| 5,833,644 A | 11/1998 | Zadno-Azizi et al. |
| 5,833,650 A | 11/1998 | Imran |
| 5,843,022 A | 12/1998 | Willard et al. |
| 5,865,721 A | 2/1999 | Andrews et al. |
| 5,908,405 A | 6/1999 | Imran et al. |
| 5,925,016 A | 7/1999 | Chornenky et al. |
| 5,938,672 A | 8/1999 | Nash |
| 5,997,558 A | 12/1999 | Nash |
| 6,021,340 A | 2/2000 | Randolph et al. |
| 6,022,336 A | 2/2000 | Zadno-Azizi et al. |
| 6,050,972 A | 4/2000 | Zadno-Azizi et al. |
| 6,080,170 A | 6/2000 | Nash et al. |
| 6,135,991 A | 10/2000 | Muni et al. |
| 6,146,372 A | 11/2000 | Leschinsky et al. |
| 6,159,195 A | 12/2000 | Ha et al. |
| 6,171,328 B1 | 1/2001 | Addis |
| 6,176,844 B1 | 1/2001 | Lee |
| 6,203,561 B1 | 3/2001 | Ramee et al. |
| 6,217,567 B1 | 4/2001 | Zadno-Azizi et al. |
| 6,231,588 B1 | 5/2001 | Zadno-Azizi |
| 6,234,448 B1 * | 5/2001 | Porat ............................ 251/10 |
| 6,241,706 B1 | 6/2001 | Leschinsky et al. |
| 6,245,008 B1 | 6/2001 | Leschinsky et al. |
| 6,245,089 B1 | 6/2001 | Daniel et al. |
| 6,248,121 B1 | 6/2001 | Nobles |
| 6,251,093 B1 * | 6/2001 | Valley et al. ............ 604/97.03 |
| 6,481,468 B1 * | 11/2002 | Taggart ........................ 141/85 |
| 6,488,801 B1 * | 12/2002 | Bodaghi et al. ............. 156/167 |
| 2002/0156486 A1 * | 10/2002 | Nadel ......................... 606/107 |

* cited by examiner

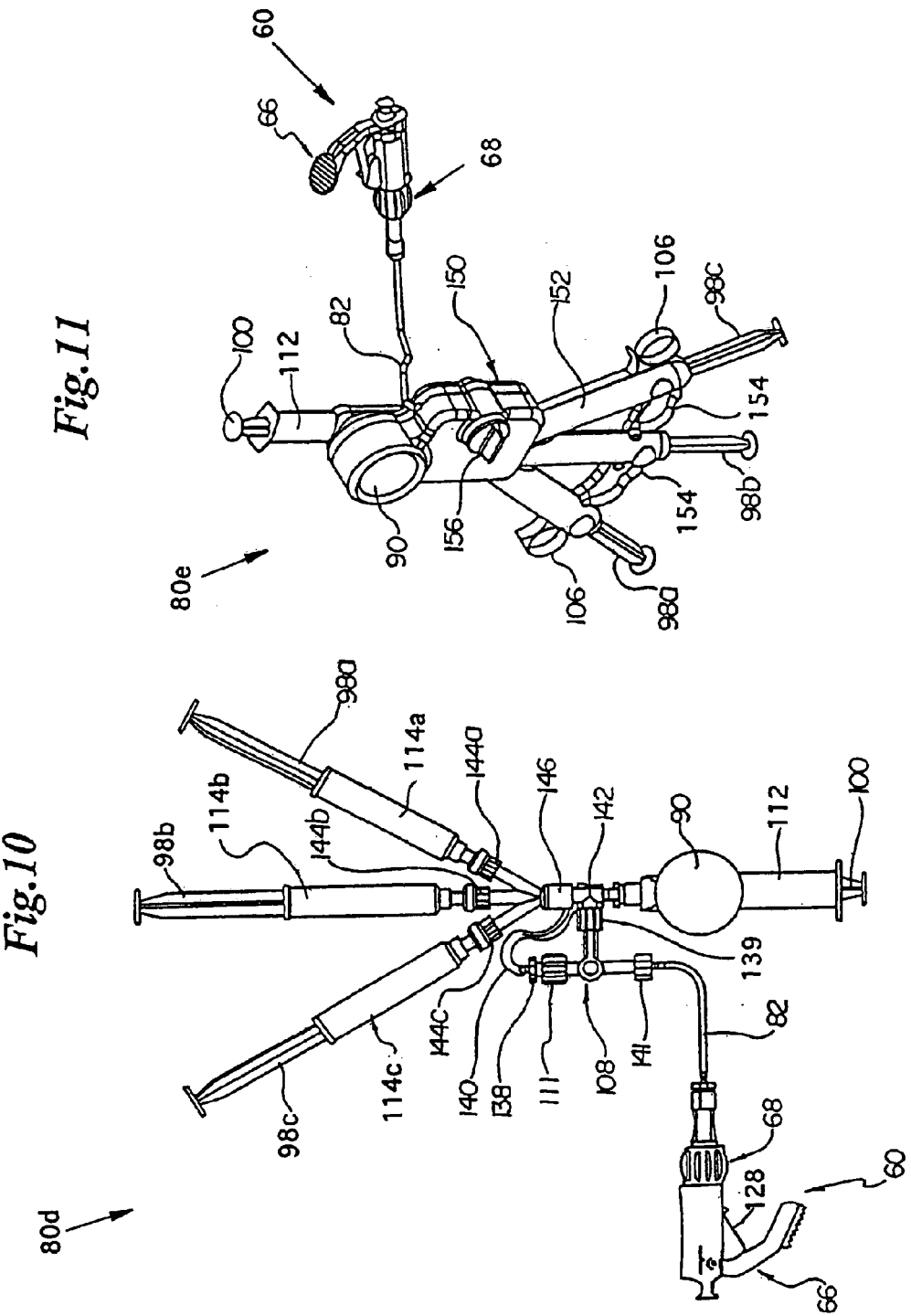

GAS INFLATION/EVACUATION SYSTEM AND SEALING SYSTEM FOR GUIDEWIRE ASSEMBLY HAVING OCCLUSIVE DEVICE

RELATED APPLICATIONS

The present invention is related to two co-pending applications that are commonly assigned to the assignee of the present invention and filed concurrently herewith, the first of which is entitled "GUIDEWIRE OCCLUSION SYSTEM UTILIZING REPEATABLY INFLATABLE GAS-FILLED OCCLUSIVE DEVICE," application Ser. No. 10/012,903, and the second of which is entitled "GUIDEWIRE ASSEMBLY HAVING OCCLUSIVE DEVICE AND REPEATABLY CRIMPABLE PROXIMAL END," application Ser. No. 10/012,891, a copy of each of which is attached and the disclosures of both of which are incorporated by reference.

FIELD OF THE INVENTION

The present invention relates generally to the field of vascular medical devices. More specifically, the present invention relates to a gas inflation/evacuation system and sealing system for selectively and repeatedly inflating an occlusive balloon and crimping an extended sealable section proximate the proximal end of a guidewire assembly during an occlusion procedure.

BACKGROUND OF THE INVENTION

Arterial disease involves damage that happens to the arteries in the body. Diseased arteries can become plugged with thrombus, plaque, or grumous material that may ultimately lead to a condition known as ischemia. Ischemia refers to a substantial reduction or loss of blood flow to the heart muscle or any other tissue that is being supplied by the artery and can lead to permanent damage of the affected region. While arterial disease is most commonly associated with the formation of hard plaque and coronary artery disease in the heart, similar damage can happen to many other vessels in the body, such as the peripheral vessels, cerebral vessels, due to the buildup of hard plaque or softer thrombus or grumous material within the lumen of an artery or vein.

A variety of vascular medical devices and procedures have been developed to treat diseased vessels. The current standard procedures include bypass surgery (where a new blood vessel is grafted around a narrowed or blocked artery) and several different types of non-surgical interventional vascular medical procedures, including angioplasty (where a balloon on a catheter is inflated inside a narrowed or blocked portion of an artery in an attempt to push back plaque or thrombotic material), stenting (where a metal mesh tube is expanded against a narrowed or blocked portion of an artery to hold back plaque or thrombotic material), and debulking techniques in the form of atherectomy (where some type of high speed or high power mechanism is used to dislodge hardened plaque) or thrombectomy (where some type of mechanism or infused fluid is used to dislodge grumous or thrombotic material). In each of these interventional vascular medical procedures, a very flexible guidewire is routed through the patient's vascular system to a desired treatment location and then a catheter that includes a device on the distal end appropriate for the given procedure is tracked along the guidewire to the treatment location.

Although interventional vascular procedures avoid many of the complications involved in surgery, there is a possibility of complications if some of the plaque, thrombus or other material breaks free and flows downstream in the artery or other vessel, potentially causing a stroke, a myocardial infarction (heart attack), or other tissue death. One solution to this potential complication is to use some kind of occlusive device to block or screen the blood flowing downstream of the treatment location. Examples of catheter arrangements that use a pair of balloons as occlusive devices to create an isolated space in the blood vessel are described in U.S. Pat. Nos. 4,573,966, 4,636,195, 5,059,178, 5,320,604, 5,833,644, 5,925,016, 6,022,336 and 6,176,844. Examples of catheter arrangements that use a single balloon as an occlusive device either upstream or downstream of the treatment location are described in U.S. Pat. Nos. 5,171,221, 5,195,955, 5,135,482, 5,380,284, 5,688,234, 5,713,917, 5,775,327, 5,792,179, 5,807,330, 5,833,650, 5,843,022, 6,021,340, 6,159,195 and 6,248,121. An example of a catheter arrangement that uses a mechanically-expanded occlusive device is shown in U.S. Pat. No. 6,231,588. Occlusive balloons also have been used on non-over-the-wire catheters without any guidewire internal to the catheter as described, for example, in U.S. Pat. Nos. 4,838,268 and 5,209,727.

The use of an occlusive device as part of a vascular procedure is becoming more common in debulking procedures performed on heart bypass vessels. Most heart bypass vessels are harvested and transplanted from the saphenous vein located along the inside of the patient's leg. The saphenous vein is a long, straight vein that has a capacity more than adequate to support the blood flow needs of the heart. Once transplanted, the saphenous vein is subject to a buildup of plaque or thrombotic materials in the grafted arterial lumen. Unfortunately, the standard interventional vascular treatments for debulking are only moderately successful when employed to treat saphenous vein coronary bypass grafts. The complication rate for a standard balloon angioplasty procedure in a saphenous vein coronary bypass graft is higher than in a native vessel with the complications including embolization, "no-reflow" phenomena, and procedural related myocardial infarction. Atherectomy methods including directional, rotational, and laser devices are also associated with a high degree of embolization resulting in a greater likelihood of infarction. The use of stents for saphenous vein coronary bypass grafts has produced mixed results. Stents provide for less restenosis, but they do not eliminate the risk of embolization and infarction incurred by standard balloon angioplasty.

In order to overcome the shortcomings of these standard non-surgical interventional treatments in treating saphenous vein coronary bypass graft occlusion, embolic protection methods utilizing a protective device distal to the lesion have been developed. The protective device is typically a filter or a balloon. Use of a protective device in conjunction with an atherectomy or thrombectomy device is intended to prevent emboli from migrating beyond the protective device and to allow the embolic particles to be removed, thereby subsequently reducing the risk of myocardial infarction. When the occlusive device is a balloon, the balloon is inserted and inflated at a point distal to the treatment site or lesion site. Therapy is then performed at the treatment site and the balloon acts to block all blood flow which prevents emboli from traveling beyond the balloon. Following treatment, some form of particle removal device must be used to remove the dislodged emboli prior to balloon deflation. U.S. Pat. No. 5,843,022 uses a balloon to occlude the vessel distal to a lesion or blockage site. The occlusion is treated with a high pressure water jet, and the fluid and entrained emboli are subsequently removed via an extraction tube. U.S. Pat. No. 6,135,991 describes the use of a balloon to occlude the vessel allowing blood flow and pressure to prevent the migration of emboli proximally from the treatment device.

There are various designs that have included an occlusive balloon on the end of a guidewire. U.S. Pat. Nos. 5,520,645, 5,779,688 and 5,908,405 describe guidewires having removable occlusive balloons on a distal end. U.S. Pat. No. 4,573,470 describes a guidewire having an occlusive balloon where the guidewire is bonded inside the catheter as an integral unit. U.S. Pat. Nos. 5,059,176, 5,167,239, 5,520, 645, 5,779,688 and 6,050,972 describe various guidewires with balloons at the distal end in which a valve arrangement is used to inflate and/or deflate the balloon. U.S. Pat. No. 5,908,405 describes an arrangement with a removable balloon member that can be repeatedly inserted into and withdrawn from a guidewire. U.S. Pat. No. 5,776,100 describes a guidewire with an occlusive balloon adhesively bonded to the distal end with an adapter on the proximal end to provide inflation fluid for the occlusive balloon.

Except in the case of the normal cerebral anatomy where there are redundant arteries supplying blood to the same tissue, one of the problems with using an occlusive device in the arteries is that tissue downstream of the occlusive device can be damaged due to the lack of blood flow. Consequently, an occlusive device that completely blocks the artery can only be deployed for a relatively short period of time. To overcome this disadvantage, most of the recent development in relation to occlusive devices has focused on devices that screen the blood through a filter arrangement. U.S. Pat. Nos. 5,827,324, 5,938,672, 5,997,558, 6,080,170, 6,171,328, 6,203,561 and 6,245,089 describe various examples of filter arrangements that are to be deployed on the distal end of a catheter system. While a filter arrangement is theoretically a better solution than an occlusive device, in practice such filter arrangements often become plugged, effectively turning the filter into an occlusive device. The filter arrangements also are mechanically and operationally more complicated than an occlusive balloon device in terms of deployment and extraction.

As is the case in almost all angioplasty devices or stenting catheter devices where a balloon is used to expand the blood vessel or stent, most catheter occlusive balloons as well as most guidewire occlusive balloons utilize a liquid fluid such as saline or saline mixed with a radiopaque marker for fluoroscopic visualization (i.e., contrast) as the inflation medium. Generally, a liquid fluid medium for expanding vascular balloons has been preferred because the expansion characteristics of a liquid are more uniform and predictable, and because a liquid medium is easier to work with and more familiar to the doctors. In the case of angioplasty balloons, for example, high-pressure requirements (up to 20 atmospheres) necessitate that the inflation fluid be an incompressible fluid for safety reasons. While having numerous advantages, liquid fluids do not lend themselves to rapid deflation of an occlusive balloon because of the high resistance to movement of the liquid in a long small diameter tube. In the context of angioplasty procedures, the balloon catheter has a much larger lumen than a guidewire. Consequently, rapid deflation is possible. In the context of a guidewire, however, liquid filled occlusive balloons typically cannot be deflated in less than a minute and, depending upon the length of the guidewire, can take up to several minutes to deflate. Consequently, it is not practical to shorten the period of total blockage of a vessel by repeatedly deflating and then re-inflating a liquid filled occlusive balloon at the end of a guidewire.

Gas-filled balloons have been used for intra-aortic occlusive devices where rapid inflation and deflation of the occlusive device is required. Examples of such intra-aortic occlusive devices are shown in U.S. Pat. Nos. 4,646,719, 4,733,652, 5,865,721, 6,146,372, 6,245,008 and 6,241,706. While effective for use as an intra-aortic occlusive device, these occlusive devices are not designed for use as a guidewire as there is no ability to track a catheter over the intra-aortic occlusive device.

An early catheter balloon device that utilized a gas as an inflation medium and provided a volume limited syringe injection system is described in U.S. Pat. No. 4,865,587. More recently, a gas-filled occlusive balloon on a guidewire is described as one of the alternate embodiments in U.S. Pat. No. 6,217,567. The only suggestion for how the guidewire of the alternate embodiment is sealed is a valve type arrangement similar to the valve arrangement used in a liquid fluid embodiment. A similar gas-filled occlusive balloon has been described with respect to the Aegis Vortex™ system developed by Kensey Nash Corporation. In both U.S. Pat. No. 6,217,567 and the Aegis Vortex™ system, the gas-filled occlusive balloon is used for distal protection to minimize the risk of embolization while treating a blocked saphenous vein coronary bypass graft. Once deployed, the occlusive balloon retains emboli dislodged by the atherectomy treatment process until such time as the emboli can be aspirated from the vessel. No specific apparatus are shown or described for how the gas is to be introduced into the device or how the occlusive balloon is deflated.

Although the use of occlusive devices has become more common for distal embolization protection in vascular procedures, particularly for treating a blocked saphenous vein coronary bypass graft, all of the existing approaches have significant drawbacks that can limit their effectiveness. Liquid filled occlusive balloons can remain in place too long and take too long to deflate, increasing the risk of damages downstream of the occlusion. Occlusive filters are designed to address this problem, but suffer from blockage problems and can be,complicated to deploy and retrieve and may allow small embolic particles to migrate downstream. Existing gas-filled occlusive balloons solve some of the problems of liquid filled occlusive balloons, but typically have utilized complicated valve and connection arrangements. It would be desirable to provide for an occlusive device that was effective, simple, quick to deploy and deflate, and that could overcome the limitations of the existing approaches.

SUMMARY OF THE INVENTION

The present invention is a gas inflation/evacuation system and sealing system for use with occlusive devices in vascular procedures. The gas inflation/evacuation system is removably connectible to the proximal end of a tubular guidewire assembly that has a distal portion and a proximal portion with an extended sealable section and includes an evacuation syringe to evacuate the tubular guidewire assembly and an inflation syringe or syringes for introducing a gas under pressure into the tubular guidewire assembly to inflate an occlusive balloon or other occlusive device proximate the distal end of the tubular guidewire assembly a plurality of times. A sealing system is also removably connectible to the proximal end of the tubular guidewire assembly and selectively seals the tubular guidewire assembly at one of a plurality of separate locations along the extended sealable section to form an airtight seal of the tubular guidewire assembly. Each time a deflation of the occlusive balloon is desired in order to reestablish blood flow to the vessel downstream of the occlusive balloon, the proximal end of the extended sealable section preferably is cut distal to the location of the last seal to quickly deflate the occlusive balloon.

The advantage of the gas inflation/evacuation system and sealing system of the present invention is that the occlusive device can be repeatably inflated and deflated a plurality of times during a vascular procedure in between which the proximal end of the tubular guidewire assembly is free of mechanical connections and obstructions and, therefore, the tubular guidewire assembly can function as a conventional exchange guidewire assembly for one or more over-the-wire catheters. Alternatively, the tubular guidewire assembly can be shorter in length for use with rapid exchange catheter systems. Unlike operation of existing liquid filled occlusive devices, the present invention enables repeated and quick inflation and deflation which allows an operator to deploy the gas-filled occlusive device numerous times during a procedure for shorter periods of time, thereby reducing the risk of potential damage to downstream tissue. Unlike operation of other gas-filled occlusive devices, the simplicity of the present invention permits the tubular guidewire assembly to be used as a conventional exchange guidewire assembly. There are no complicated mechanical arrangements or valve systems internal to the tubular guidewire assembly that increase the cost, complexity, and potential for failure of the system.

In a preferred embodiment, the extended sealable section is an extended crimpable section and the sealing system includes a crimping mechanism. The extended crimpable section has a sufficient length to permit a plurality of crimps and cuts along the extended crimpable section and preferably has an outer diameter that is smaller than the outer diameter of the main body portion of the guidewire assembly. The crimping mechanism is used to crimp the extended crimpable section of the guidewire assembly to seal the guidewire assembly a plurality of times. Preferably, the gas inflation/evacuation system and the crimping mechanism and sealing mechanism of the sealing system constitute a handheld apparatus. Each time a deflation of the occlusive device is desired in order to reestablish blood flow to the vessel downstream of the occlusive device, the extended crimpable section is cut distal to the location of the last crimp so as to quickly deflate the occlusive device. Preferably, the extended crimpable section of the guidewire assembly is dimensioned and the crimping mechanism is arranged such that an effective outer diameter of the extended crimpable section at the location of a seal is no greater than the outer diameter of the main body portion of the guidewire assembly when the extended crimpable section is sealed.

In an alternate embodiment, the sealing mechanism is a plugging mechanism that selectively inserts a plug of material into the proximal end of the extended sealable section while maintaining an airtight seal between the guidewire assembly and the gas inflation/evacuation system. In one embodiment, the plug of material includes a wax/gel material and the sealing system includes wiping structure to remove excess wax/gel material from the outside of the extended sealable section once the wax/gel material has been inserted. In this embodiment, the extended sealable section may be opened either by cutting the extended sealable section distal to the location of the seal or by heating the proximal end of the extended sealable section.

In one embodiment for coronary vascular procedures, the guidewire assembly preferably has an effective length of at least 40 cm and more preferably at least 100 cm and an outer diameter of less than 0.060 inch and more preferably less than 0.018 inch, the extended sealable section has an effective length of at least 1 cm and more preferably at least 5 cm and an outer diameter of less than 0.050 inch and more preferably less than 0.012 inch, and the occlusive device (balloon) is deflated in less than two minutes and more preferably less than one minute. This embodiment is particularly adapted to provide distal embolization protection in debulking vascular interventional procedures, such as those involving a blocked saphenous vein coronary bypass graft. Alternatively, the guidewire assembly may be configured and dimensioned for use in peripheral vascular procedures or neurovascular procedures.

In a preferred embodiment, the inflation system of the gas inflation/evacuation system includes a plurality of individually actuatable syringes each containing a sufficient volume of biocompatible gas for a single inflation of the occlusive device so as to minimize the volume of biocompatible gas in the gas inflation/evacuation system in the event of a leak. The preferred embodiment is packaged in a sterile packaging that is assembled and packaged in a sealed chamber filled with a biocompatible gas such that any gas within the sterile packaging once packaged is only the biocompatible gas.

BRIEF DESCRIPTION OF THE DRAWINGS

FIGS. 4a and 4b are fragmentary cross-sectional views of different manners of joining the extended sealable section to the main body portion at the proximal portion of the guidewire assembly of FIG. 3a.

FIG. 10 is a top view of a preferred embodiment of a gas inflation/evacuation system and sealing system of the present invention.

FIG. 11 is a perspective view of another alternate embodiment of a gas inflation/evacuation system and sealing system.

DETAILED DESCRIPTION OF THE PREFERRED EMBODIMENTS

Figure 1:
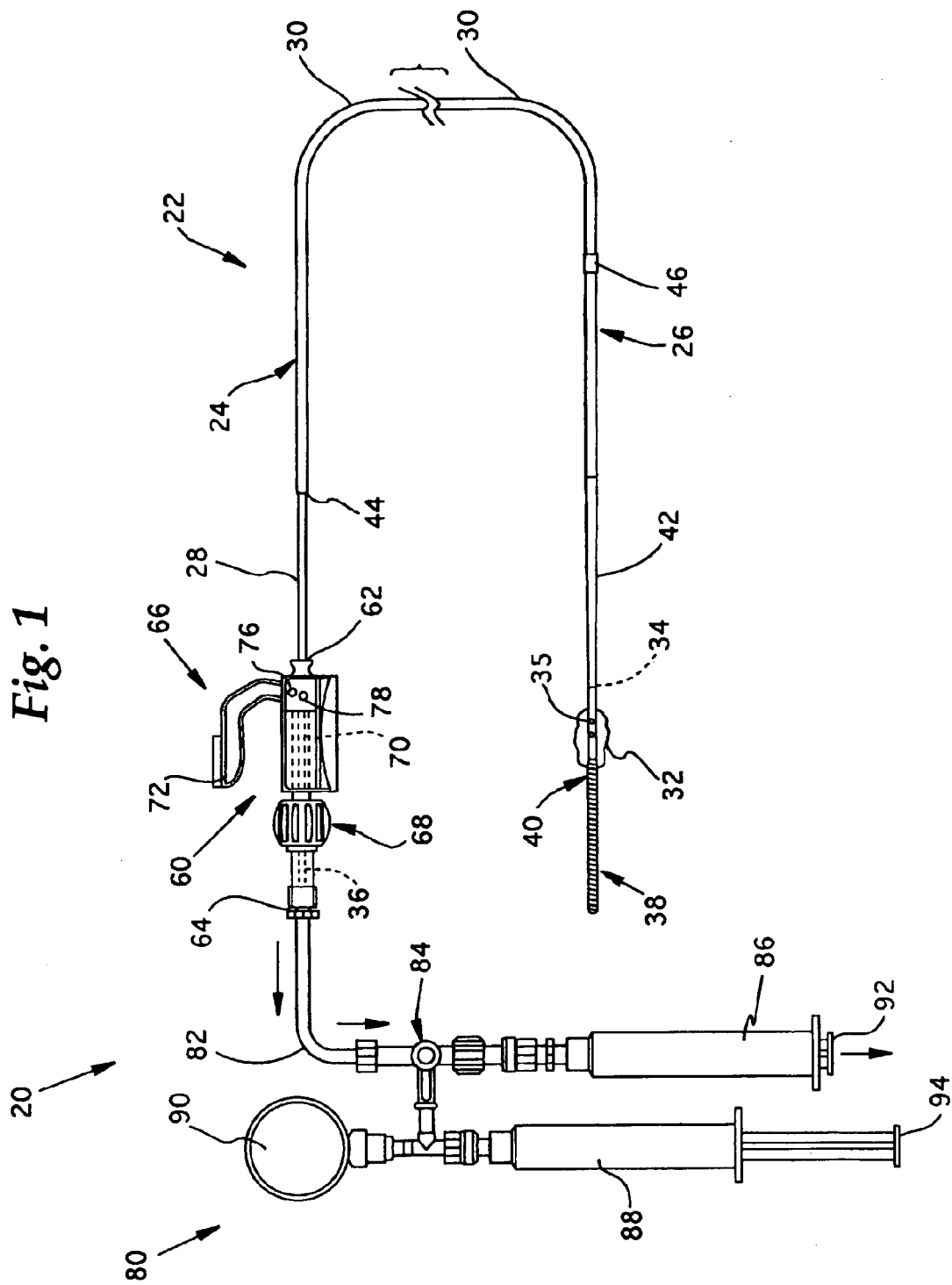
FIG. 1 is a schematic diagram of a guidewire occlusion system incorporating the present invention and operating in an evacuation mode.
Figure 2:
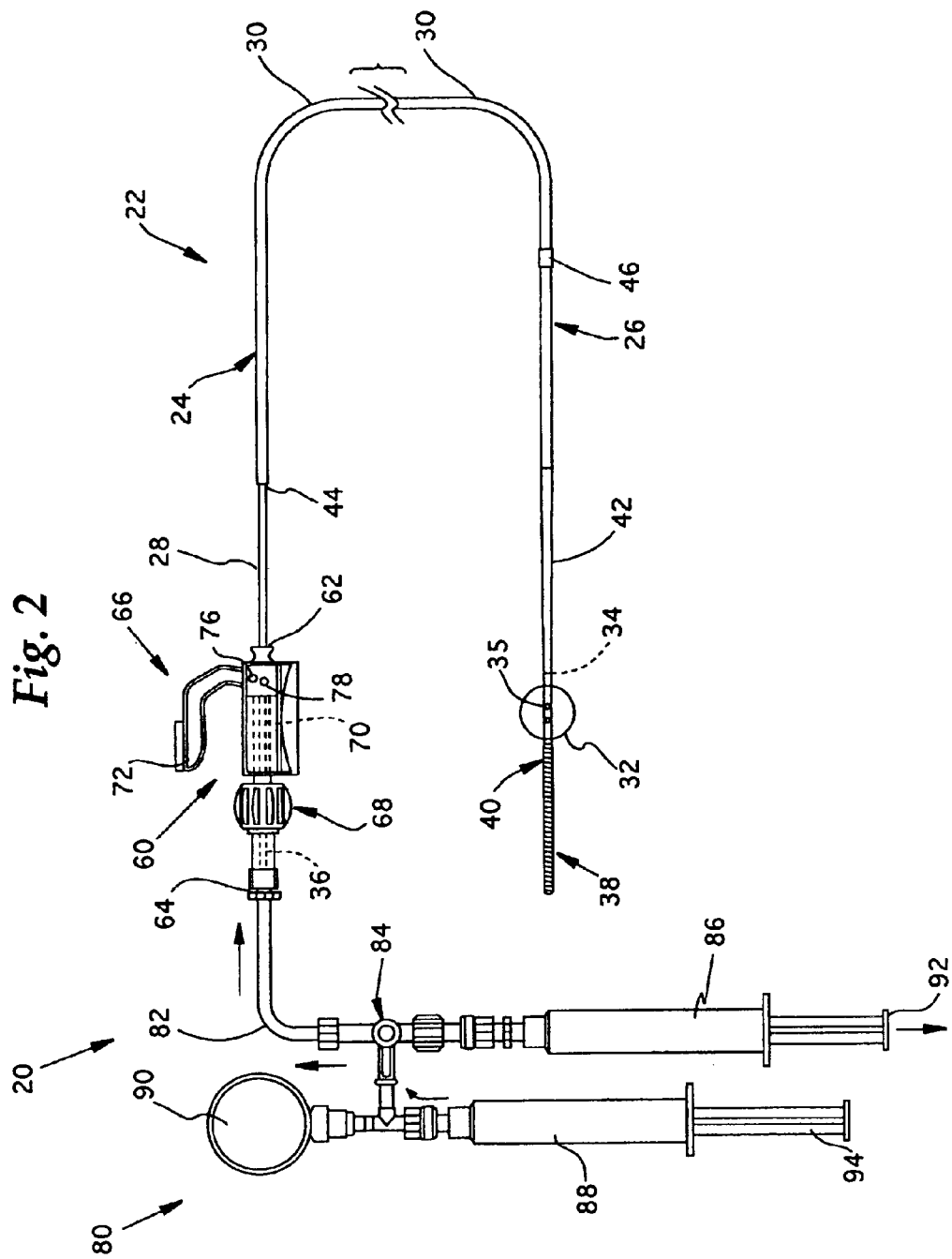
FIG. 2 is a schematic diagram of the guidewire occlusion system shown in FIG. 1 operating in an inflation mode.
Figure 3A:
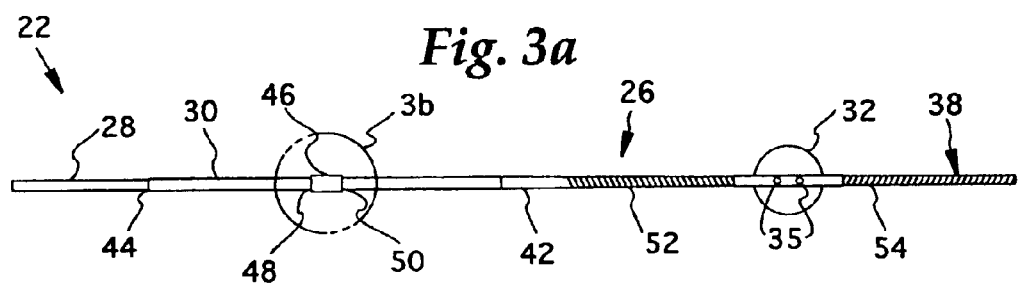
FIG. 3a is a side view of the guidewire assembly shown in FIG. 1.
Figure 3B:
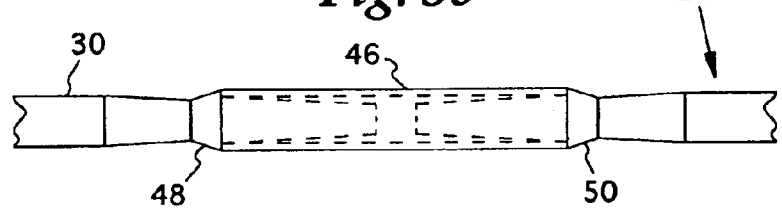
FIG. 3b is an enlarged view of the portion of FIG. 3a delineated by the circle 3b.

Referring now to FIGS. 1–2, the overall structure and operation of a guidewire occlusion system 20 incorporating the present invention will be described. The guidewire occlusion system 20 includes a guidewire assembly 22, a sealing system 60, and a gas inflation/evacuation system 80. The preferred embodiments of the overall guidewire occlusion system 20 are described in further detail in the previously identified co-pending application Ser. No. 10/012,903 entitled "Guidewire Occlusion System Utilizing Repeatably Inflatable Gas-Filled Occlusive Device".

Guidewire assembly 22 is a tubular member that includes a proximal portion 24 and a distal portion 26. As used in the present invention, the terms proximal and distal will be used with reference to an operator, such that a distal portion of the guidewire assembly 22, for example, is the portion first inserted into a blood vessel, and the proximal portion remains exterior to the patient and is therefore closer to the operator. An extended sealable section 28 is provided proximate the proximal portion 24 of guidewire assembly 22. Preferably, the extended sealable section 28 is an extended crimpable section comprised of a tubular segment having an outer diameter smaller than an outer diameter of a main body portion 30 of guidewire assembly 22. Although the diameter of the extended crimpable section could be any size consistent with effective use as a guidewire, it will be understood that the smaller diameter allows for less force to be used in sealing the extended crimpable section and provides a crimped seal that is not too large when crimped. An occlusive balloon 32 is located along the distal portion 26 of guidewire assembly 22. The occlusive balloon 32 is fluidly connected via a lumen 34 to the proximal end 36 of guidewire assembly 22, with channels or holes 35 allowing for fluid communication between lumen 34 and occlusive balloon 32. In a preferred embodiment, a flexible tip 38 is positioned at the distal end 40 of distal portion 26 of the guidewire assembly 22. Preferably, distal portion 26 of guidewire assembly 22 includes a tapered portion 42 to increase the flexibility and transition properties of the distal portion 26 of guidewire assembly 22.

Preferably, sealing system 60 is implemented as part of a handheld apparatus that also includes gas inflation/evacuation system 80. Alternatively, sealing system 60 may be a handheld unit completely separate from the gas inflation/evacuation system 80. Sealing system 60 includes a first aperture 62 into which the proximal end 36 of guidewire assembly 22 is insertable so as to operably position at least a portion of extended sealable section 28 in relation to sealing system 60. Sealing system 60 further includes a second aperture 64 that is fluidly connectible to gas inflation/evacuation system 80. The sealing system 60 includes means for selectively sealing the extended sealable section which in the preferred embodiment comprises a crimping mechanism 66 and a sealing mechanism 68. A passageway 70 is defined from first aperture 62 to second aperture 64 and extends through both crimping mechanism 66 and sealing mechanism 68. Preferably, at least a portion of the extended sealable section 28 is inserted into first aperture 62 a sufficient distance to engage crimping mechanism 66 and sealing mechanism 68.

Figure 12:
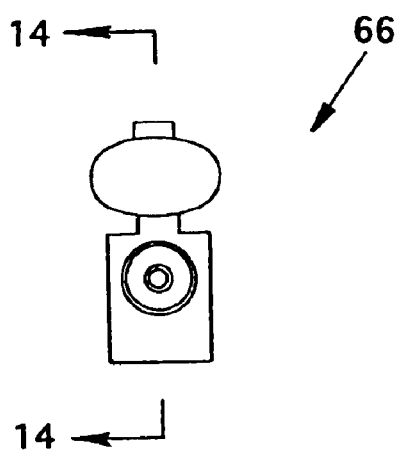
FIG. 12 is an end view of a crimping mechanism.
Figure 13:
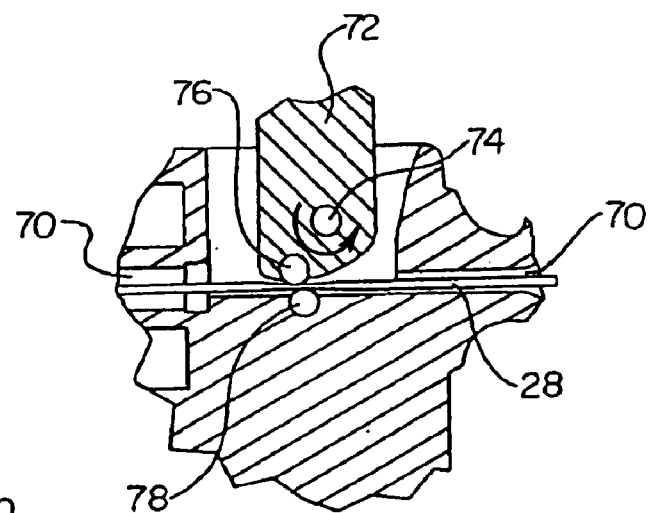
FIGS. 13 and 14 are two sectional views of the crimping mechanism of FIG. 12, FIG. 14 being a view taken along the line 14—14 of FIG. 12, and FIG. 13 being a magnification of the portion of FIG. 14 indicated by the dashed circle.
Figure 14:
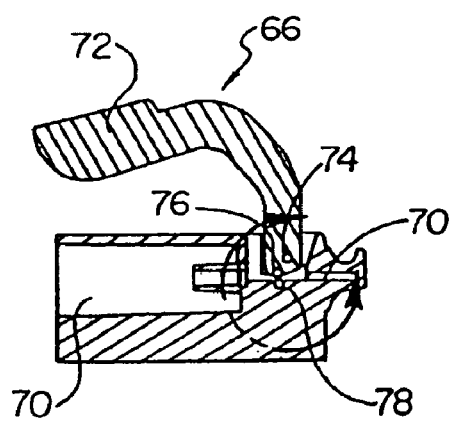

In a preferred embodiment of the crimping mechanism 66 as shown in FIGS. 12–14, the crimping mechanism 66 comprises a handle 72 that actuates a pivotable cam arrangement 74 that crimps and then severs the extended sealable section 28 between a pair of rollers 76, 78 by mechanically flattening and pinching the extended sealable section 28 to the point of breaking. Preferably, the sealing mechanism 68 has a rotatable hemostatic valve positioned proximal to the crimping mechanism 66 along passageway 70. Preferably, crimping mechanism 66 and sealing mechanism 68 are arranged coaxially with each other along a straight portion of passageway 70. In this embodiment, when the proximal end 36 of guidewire assembly 22 is inserted into first aperture 62 until the proximal end 36 engages the hemostatic valve of sealing mechanism 68, the extended sealable section 28 is properly positioned relative to the crimping mechanism 66.

It will be seen that the relative distance between the engaging portions of sealing mechanism 68 and crimping mechanism 66 in this embodiment effectively defines the relative distances between a plurality of locations along extended sealable section 28 at which an airtight seal can be created, as shown in FIGS. 1–2. To permit multiple inflations and deflations of the occlusive balloon 32 of the guidewire assembly 22, the length of the extended sealable section 28 should be greater than at least twice the distance between crimping mechanism 66 and sealing mechanism 68.

The gas inflation/evacuation system 80 is connected via conduit 82 to the second aperture 64 of the sealing system 60. The gas inflation/evacuation system 80 preferably includes a valve arrangement 84 that selectively couples one of an evacuation system which includes means for evacuating the guidewire assembly 22 and an inflation system which includes means for introducing a gas into the guidewire assembly 22 to the conduit 82. The evacuation system includes an evacuation syringe 86 which is used to evacuate the guidewire assembly 22, passageway 70, and conduit 82. The inflation system includes an inflation syringe 88 which contains a volume of a biocompatible gas sufficient to inflate the occlusive balloon 32 a plurality of times. Preferably, the biocompatible gas is carbon dioxide. Other biocompatible gasses that may be utilized with the present invention include oxygen, nitrogen, and nitrous oxide. Although not preferred, low viscosity biocompatible liquids or foams also may be used for inflation provided the surface tension of the fluid is sufficient to permit the rapid inflation and deflation contemplated by the present invention. Optionally, a pressure gauge 90 can be associated with the inflation syringe 88.

Figure 4A:
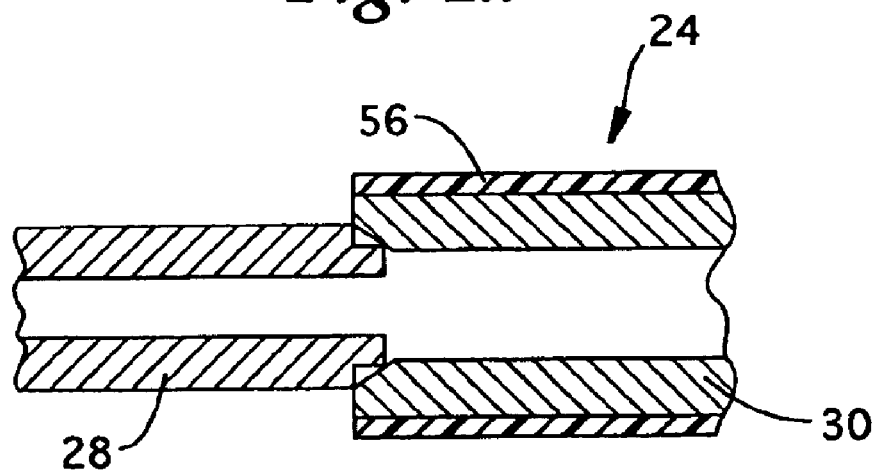
Figure 4B:
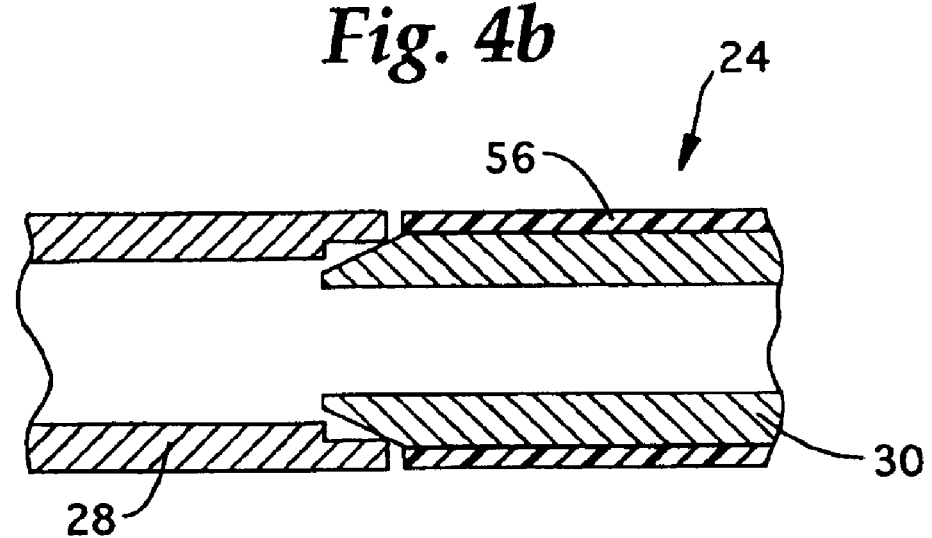

In a preferred embodiment shown in FIGS. 3a, 3b, 4a and 4b, guidewire assembly 22 is constructed as described in further detail in the previously identified co-pending application Ser. No. 10/012,891 entitled "Guidewire Assembly Having Occlusive Device And Repeatably. Crimpable Proximal End." The main body portion 30 is formed of a primary stainless steel hypotube having an outer diameter of 0.013 inch and an inner diameter of 0.007 inch. To accomplish passive deflation in the desired time of less than one minute when the extended sealable section 28 is cut, it is preferable that the main body portion 30 have an inner diameter of at least 0.002 inch. The extended sealable section 28 of guidewire assembly 22 is comprised of a crimp tube also formed of stainless steel and having an outer diameter of 0.009 inch to 0.015 inch and an inner diameter of at least 0.002 inch and preferably about 0.005 inch. The extended sealable section 28 is preferably a separate piece secured to the proximal portion 24 by a laser weld 44 (see FIGS. 1, 2 and 3a) of sufficient strength. Alternatively, the extended sealable section 28 may be formed by centerless grinding or reducing the outer diameter of a portion of the proximal portion 24 of the main body portion 30 of guidewire assembly 22. Still other embodiments may enable the extended sealable section to be a modified, treated or otherwise fabricated portion of the proximal portion 24 of the main body portion 30 of guidewire assembly 22 that is suitable for the particular sealing technique to be used. As shown in FIG. 4a, in one embodiment the distal end of the extended sealable section 28 is preferably centerless ground and press fit within a chamfered proximal end of the main body portion 30. Alternatively, as shown in FIG. 4b, a chamfered crimp arrangement could be used. Still further, a separate joining/crimping tube or other tubular joining arrangements could be used. Preferably, a protective polymer coating 56 of polytetrafluoroethylene (PTFE) or a hydrophilic coating is applied by any of a number of known techniques such that the coating 56 surrounds the main body portion 30. The protective polymer coating 56 is preferably about 0.0004+/−0.0003 inch thick such that the effective outer diameter of the main body portion 30 of guidewire assembly 22 is 0.0132–0.0144 inch.

In this embodiment, the extended sealable section 28 can be made of any material that when deformed and severed retains that deformation so as to form an airtight seal. When crimped and severed, it is preferable that the extended sealable section 28 not present a sharp, rigid point that is capable of piercing a gloved hand. It has been found that as long as the preferred embodiment is not gripped within less than one inch of the proximal end of the extended sealable section 28, the severed proximal end of the extended sealable section 28 does not penetrate a standard surgical glove. In addition, the extended sealable section 28 must have sufficient strength in terms of high tensile and kink resistance to permit catheter devices to repeatedly pass over the extended sealable section 28.

In this embodiment, the main body portion 30 is preferably secured to the distal portion 26 using a Ni—Ti or stainless steel sleeve 46 laser welded to the main body portion 30 at laser weld 48 and crimped to the distal portion 26 at crimp 50. The distal portion 26 is preferably formed of a Ni—Ti alloy having an inner diameter of 0.0045 inch and an outer diameter that ranges from 0.014 inch to 0.0075 inch to form tapered portion 42, preferably formed by a centerless grinding process. Preferably, the distal portion includes a pair of coil sections, proximal tip coil 52 and distal tip coil 54, that are longitudinally spaced apart and adjacent to the holes 35 and that assist in providing a better surface for bonding the occlusive balloon 32 to the distal portion 26. This arrangement also tends to increase the visibility of the location of the occlusive balloon 32 under fluoroscopy, as the occlusive balloon 32 filled with a biocompatible gas will be radiotranslucent when compared to the two coils 52 and 54. Alternatively, a platinum markerband could be located around the distal portion 26 just proximal to the occlusive balloon 32 to serve as a radiopaque/MRI marker. The flexible tip 38 is a coiled tip attached to distal portion 26 distal to occlusive balloon 32, preferably by a crimp. Alternatively, a sleeve could be welded to the flexible tip 38, and the tapered portion 42 could then be inserted into this sleeve and crimped.

Alternatively, any number of other alloys or polymer materials and attachment techniques could be used in the construction of the guidewire assembly 22, provided the materials offer the flexibility and torque characteristics required for a guidewire and the attachment techniques are sufficiently strong enough and capable of making an airtight seal. These materials include, but are not limited to, Ni—Ti, 17-7 stainless steel, 304 stainless steel, cobalt superalloys, or other polymer, braided or alloy materials. The attachment techniques for constructing guidewire assembly 22 include, but are not limited to, welding, mechanical fits, adhesives, sleeve arrangements, or any combination thereof.

The occlusive balloon 32 may be made of any number of polymer or rubber materials. Preferably, the occlusive balloon is preinflated to prestretch it so that expansion is more linear with pressure. Preferably, the pressure supplied by gas inflation/evacuation system 80 is designed to stay well within the elastic limit of the occlusive balloon 32. A two-layer occlusive balloon arrangement, adding gas and/or liquid between balloon layers, may be used in an alternate embodiment to increase visibility of the distal end 40 of the distal portion 26 of the guidewire assembly 22 under fluoroscopy.

In practice, medical personnel gain entry to the vessel lumen prior to use of the guidewire occlusion system 20. The extended sealable section 28 of the proximal portion 24 of guidewire assembly 22 is inserted into first aperture 62 and connected via sealing mechanism 68. The distal portion 26 of guidewire assembly 22 is inserted into the vessel lumen, and occlusive balloon 32 is inserted to a point distal to the vessel occlusion. Valve arrangement 84 is set for evacuation. Evacuation syringe plunger 92 of evacuation syringe 86 is slidably withdrawn removing any air from guidewire assembly 22. Valve arrangement 84 is then set for inflation. Inflation syringe plunger 94 of inflation syringe 88 is slidably advanced inserting a volume of an inert gas into guidewire assembly 22. The inert gas inflates occlusive balloon 32 as shown in FIG. 2. During inflation, the medical personnel monitor pressure gauge 90 to ensure that the inflation pressure does not exceed the burst rating of the occlusive balloon 32 and to gauge the relative size of the occlusive balloon 32 as it is inflated. Following inflation of occlusive balloon 32, crimping mechanism 66 is employed to crimp the extended sealable section 28 of guidewire assembly 22, thereby sealing the guidewire assembly 22 to maintain the occlusive balloon 32 in an inflated state. Sealing mechanism 68 is released and the extended sealable section 28 is removed from first aperture 62 such that the proximal portion 24 of the guidewire assembly 22 is free of mechanical or other obstructions and can function as a conventional guidewire. When the medical personnel decide to deflate the occlusive balloon 32, the extended sealable section 28 is cut using a medical scissors or the like distal to the existing crimp in the extended sealable section 28. When the medical personnel deem reinflation of the occlusive balloon 32 to be necessary, the extended sealable section 28 of the proximal portion 24 is reinserted into first aperture 62. Sealing mechanism 68 is then reactivated and the evacuation/inflation process can be repeated. It will be understood that a crimping handle 72 may also be provided with a separate severing arrangement to cut the extended sealable section 28. Alternatively, extended sealable section 28 may be scored or otherwise weakened in selected locations to assist in crimping or severing, including severing by repeated bending back and forth at one of the scored locations. In another embodiment, the extended sealable section 28 could be broken off rather than sheared by using a brittle metal for the extended sealable section that aids in the severing of the extended sealable section 28.

Figure 5:
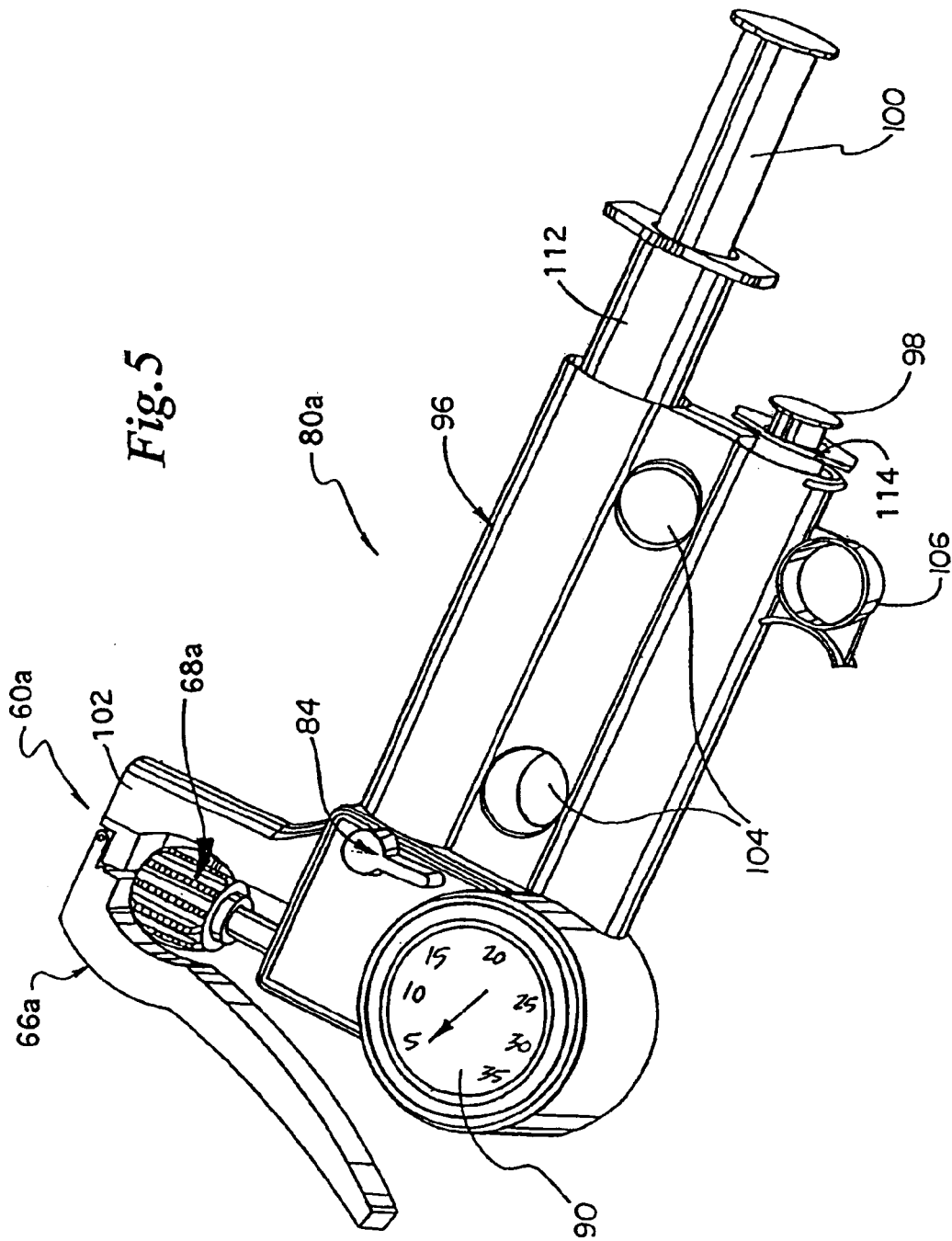
FIGS. 5–7 are perspective views of three alternate embodiments of gas inflation/evacuation systems and the sealing systems used therewith.

FIG. 5 shows an alternative unitized gas inflation/evacuation system 80a and also an alternative sealing system 60a. Assembly body 96 contains individual inflation syringe 114 with inflation syringe plunger 98 and individual evacuation syringe 112 with evacuation syringe plunger 100. Assembly body 96 contains pressure gauge 90. Attached to assembly body 96 is support structure 102 which supports a sealing system 60a that includes crimping mechanism 66a and sealing mechanism 68a. Valve arrangement 84 is mounted on the surface of assembly body 96. Assembly body 96 contains two fingergrip bores 104. Attached to assembly body 96 is fingergrip 106. In the preferred embodiment, the assembly body 96 is constructed of a suitable inert plastic polymer, although any polymer material used in construction of medical devices could be used. In another embodiment, the assembly body 96 can be constructed of suitable metal alloys or even of tempered glass or any combination thereof.

Figure 6:
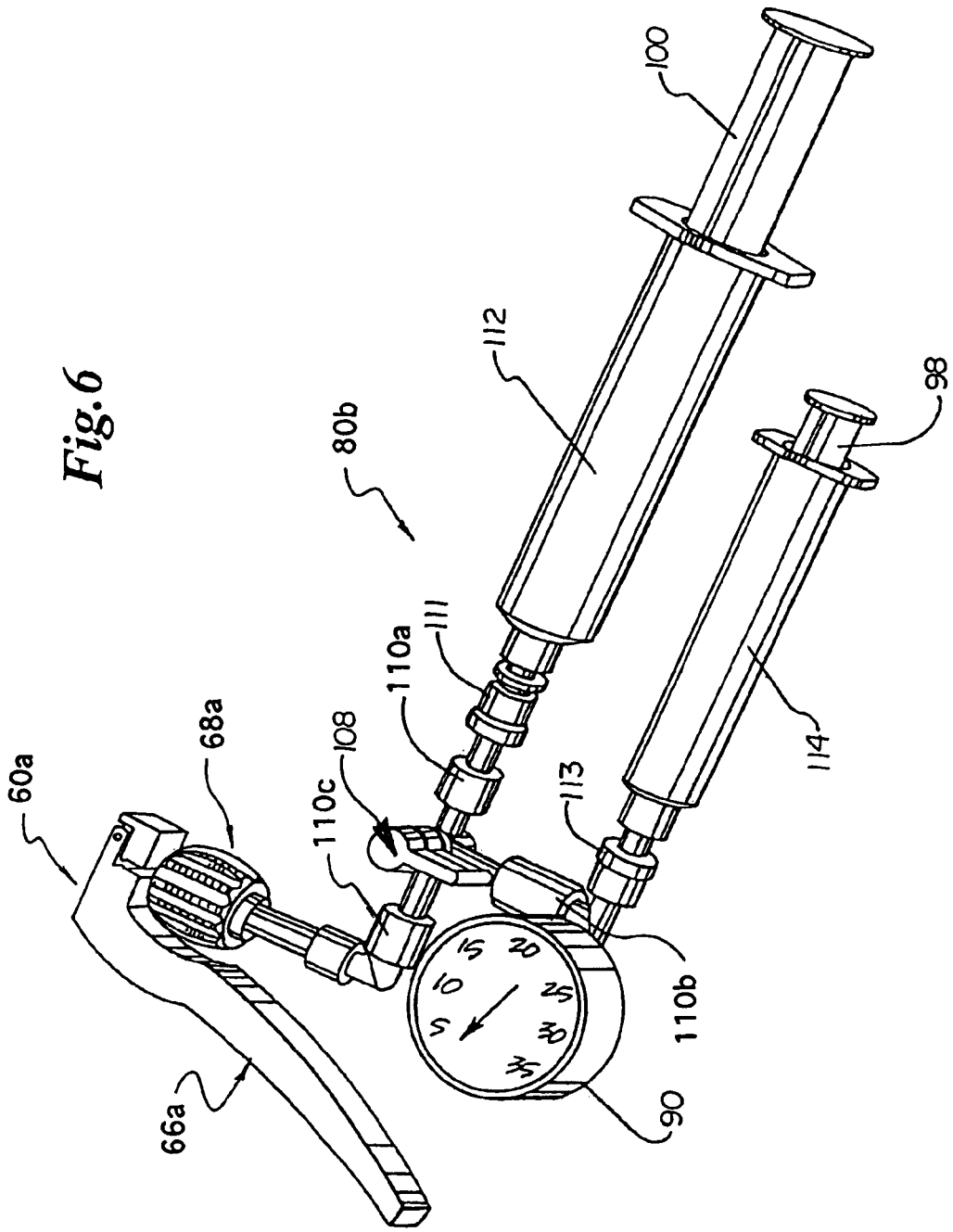

FIG. 6 shows an alternative gas inflation/evacuation system 80b in use with sealing system 60a. Valve arrangement 108 has three interconnect fittings 110a, 110b and 110c. Attached to interconnect fitting 110a is evacuation syringe 112. Evacuation syringe 112 includes evacuation syringe plunger 100. Attached to interconnect fitting 110b is pressure gauge 90. Pressure gauge 90 is fluidly interconnected to inflation syringe 114. Inflation syringe 114 includes inflation syringe plunger 98. Attached to the interconnect fitting 110c is sealing system 60a comprised of crimping mechanism 66a and sealing mechanism 68a. Preferably, one-way check valves 111 and 113 are respectively connected between interconnect fitting 110a and evacuation syringe 112 and between interconnect fitting 110b and inflation syringe 114 as a safety measure to ensure only one-way flow of the gas within the gas inflation/evacuation system 80b. One-way check valve 113 ensures that only the carbon dioxide gas is delivered out of the gas inflation/evacuation system and prevents any reinfusion of air that has been evacuated from the gas inflation/evacuation system.

Figure 7:
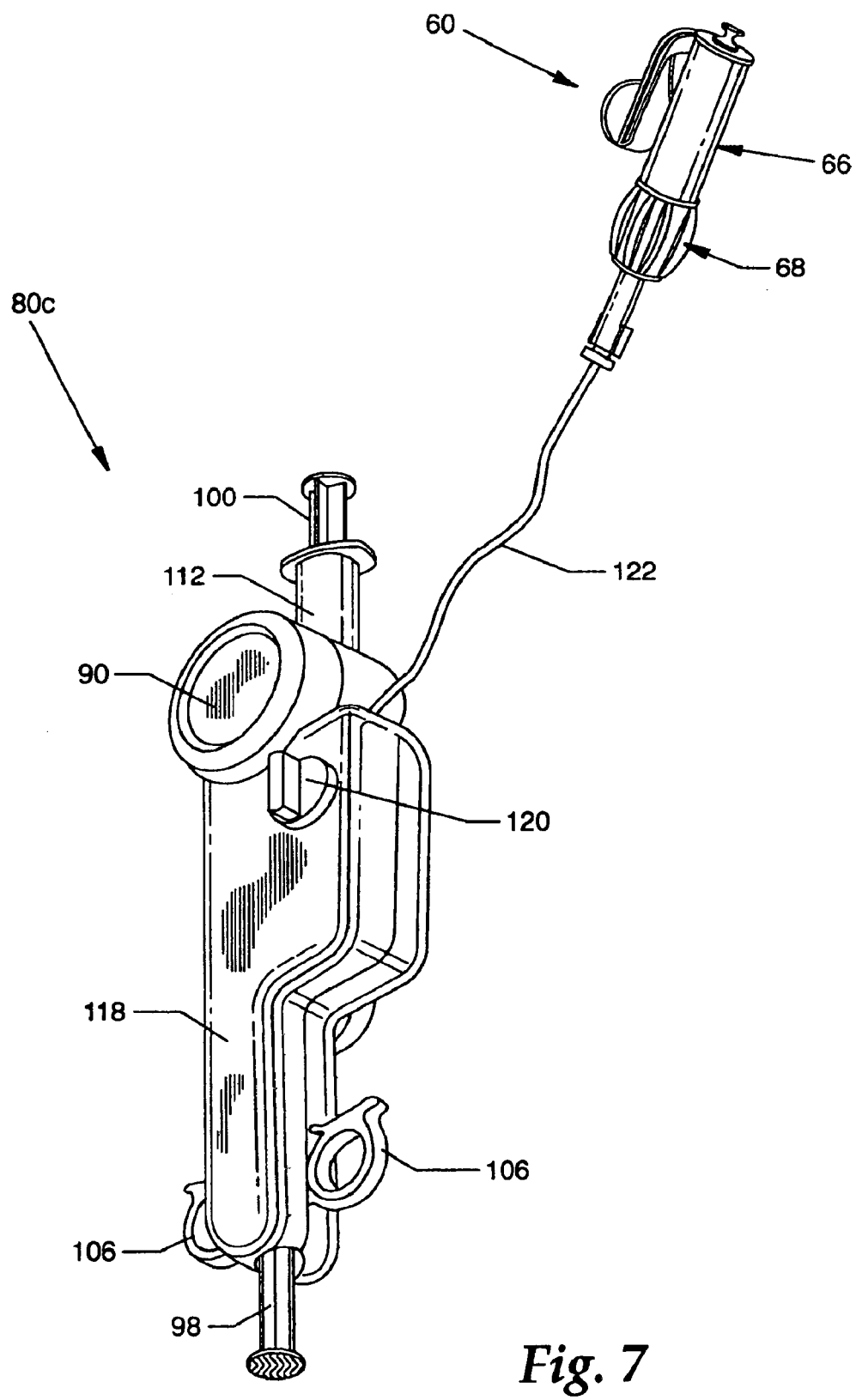
Figure 8:
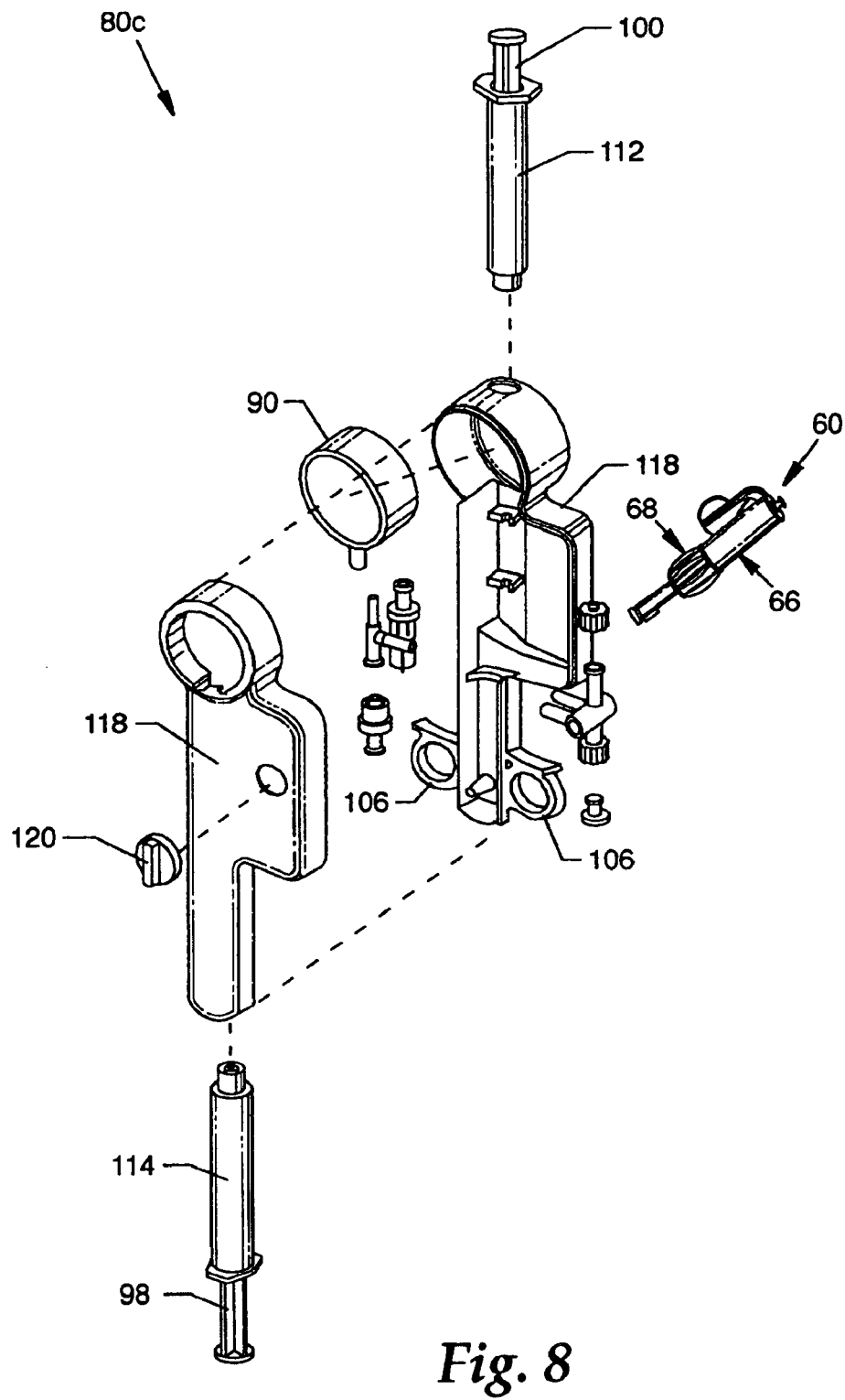
FIG. 8 is an exploded view of the gas inflation/evacuation system of the alternate embodiment shown in FIG. 7 and the associated sealing system.

FIGS. 7 and 8 show an alternative gas inflation/ evacuation system 80c with sealing system 60. Assembly body 118 contains inflation syringe 114 and evacuation syringe 112. Inflation syringe 114 includes inflation syringe plunger 98. Evacuation syringe 112 includes evacuation syringe plunger 100. Knob 120 connected to valve arrangement 108 is mounted on the exterior of assembly body 118. Pressure gauge 90 is contained within assembly body 118. Assembly body 118 contains fingergrips 106. Conduit 122 is attached to assembly body 118. At the distal end of conduit 122 is sealing system 60 which is comprised of crimping mechanism 66 and sealing mechanism 68.

Figure 9:
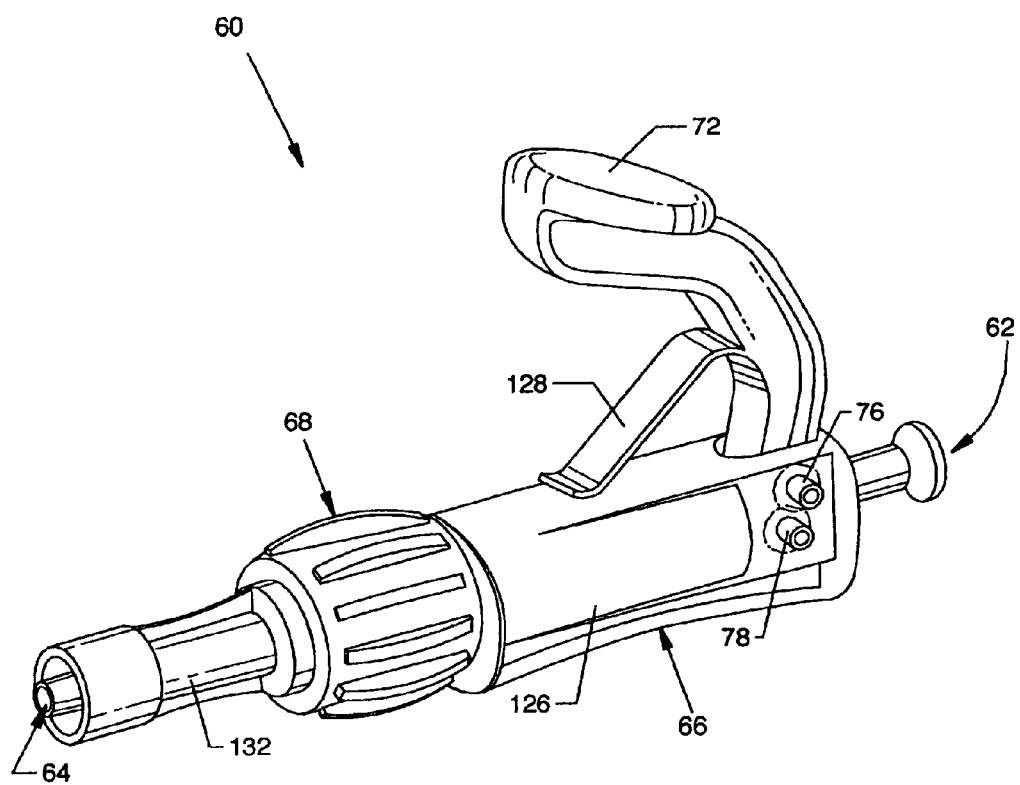
FIG. 9 is a perspective view of the sealing system illustrated with the alternate embodiment shown in FIG. 7.

FIG. 9 shows an embodiment of the sealing system. Specifically, FIG. 9 shows sealing system 60 which is comprised of sealing mechanism 68 and crimping mechanism 66. Crimping mechanism 66 is comprised of crimp body 126, handle 72, handle return 128, and first aperture 62. Sealing mechanism 68 is comprised of sealing body 132 and second aperture 64. Sealing system 60 has a passageway 70 (see FIGS. 1 and 2) fluidly interconnecting first aperture 62 and second aperture 64.

FIG. 10 shows an alternative gas inflation/evacuation assembly 80d coupled to sealing system 60. Valve arrangement 108 has a coupling 141 connected to conduit 82 and a port 138 that is attached via one-way check valve 111 and hose 140 to evacuation syringe 112. Attached to an interconnect fitting 139 of the valve arrangement 108 is inflation manifold 142. Inflation manifold 142 is connected to connector 146 and pressure gauge 90. Inflation manifold 142 has three check valves 144a, 144b and 144c. Check valves 144a, 144b and 144c are connected to respective inflation syringes 114a, 114b and 114c which have respective inflation syringe plungers 98a, 98b, and 98c. In this embodiment, evacuation syringe 112 is mounted behind pressure gauge 90. As with the other embodiments, the distal end of conduit 82 is connected to sealing system 60. Sealing system 60 is comprised of sealing mechanism 68 and crimping mechanism 66.

FIG. 11 shows an alternative gas inflation/evacuation system 80e that is similar to the gas inflation/evacuation system 80d shown in FIG. 10 except that the components are arranged in a common housing 150. Common housing 150 has internal sealed channels that fluidly interconnect via valve arrangement 108 to evacuation syringe 112 and to inflation syringes 114a, 114b and 114c and pressure gauge 90. Common housing 150 has structure 152 that defines chambers for the three inflation syringes 114a, 114b and 114c. Common housing 150 also includes structure defining external fingergrips 106 and internal fingergrips 154 between adjacent portions of structure 152. Common housing 150 also contains structure for integrating evacuation syringe 112 and pressure gauge 90 as part of the common housing 150. An external knob 156 connects to the valve arrangement 108.

Figure 19:
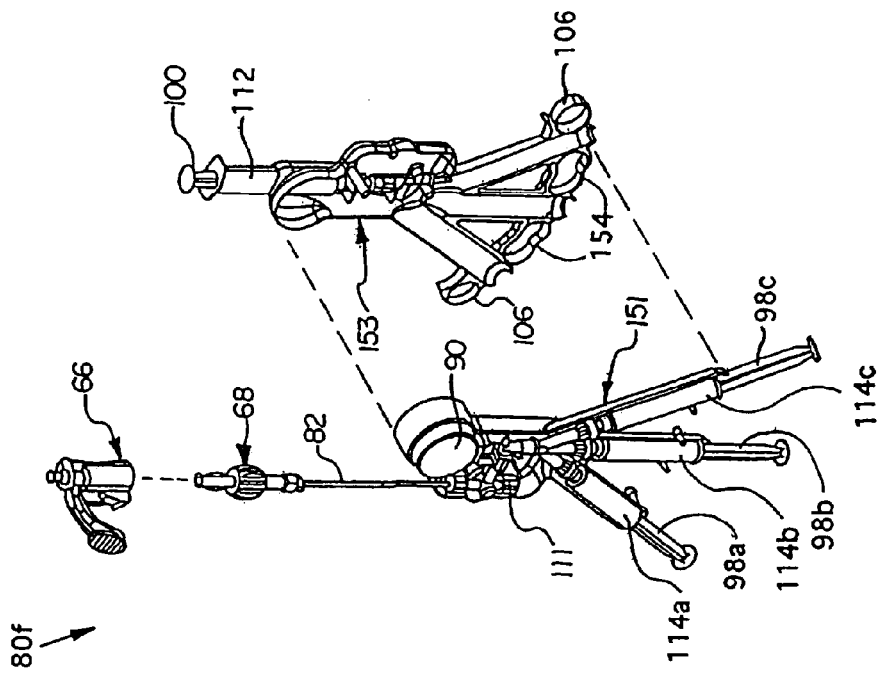
FIG. 19 is a partially exploded view of the alternate embodiment of FIG. 18 including the entire joinable housing assembly thereof.
Figure 18:
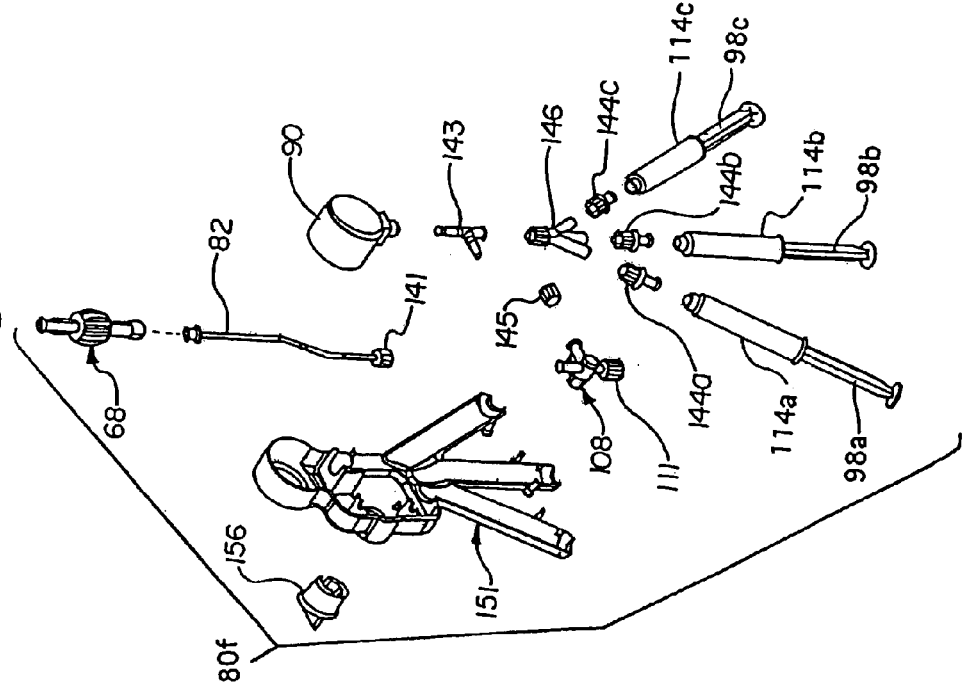
FIG. 18 is an exploded view of still another alternate embodiment of a gas inflation/evacuation system and sealing system.

FIGS. 18 and 19 show an alternative embodiment to that shown in FIG. 11. Rather than utilizing the common housing 150 with internal sealed channels, an assembled gas inflation/evacuation system 80f, substantially similar to the gas inflation/evacuation system 80d shown in FIG. 10, is securely placed within a two-part housing such that the two-part housing provides a protective and functional casing around the gas inflation/evacuation system 80f. As demonstrated in the exploded view of FIG. 18, the previously described components of the gas inflation/evacuation system 80d are assembled prior to fitting of the housing. In addition to the components described above with relation to FIG. 10, this exploded view shows two additional components: namely, tee connector 143 and coupling 145. Tee connector 143 is intermediately connected to pressure gauge 90 at one end and connector 146 at the other end. Further, coupling 145 interconnects valve arrangement 108 to tee connector 143. Upon completion of the component assembly, the assembled system is securely placed within a top housing half 151, as shown in FIG. 19. Once secured, a compatible bottom housing half 153, as also shown in FIG. 19, is joined with top housing half 151 to form the full housing. This joining of top housing half 151 and bottom housing half 153 can be achieved using a myriad of techniques, such as adhesive bonding, heat bonding, chemical bonding, pressure fittings, snap connectors, clip connectors, fasteners such as screws and bolts, and the like.

The embodiments shown in FIGS. 10, 11, 18, and 19 allow for effective pressurization of occlusive balloon 32 at less than 2 atmospheres while reducing the total volume of gas that might be introduced into a patient in the event of a leak in the guidewire occlusion system 20. Depending upon the desired inflation pressure and the total number of inflation cycles, the total amount of pressurized gas in a single inflation syringe such as 88 in FIGS. 1 and 2 or 114 in FIGS. 5–8 can be significant. If a leak were to occur, the entire contents of a single inflation syringe would be susceptible to that leak. By using a separate inflation syringe 114a, 114b, 114c for each inflation in the embodiments shown in FIGS. 10, 11, and 18 and 19, these alternate embodiments provide a simple way of decreasing the total amount of pressurized gas that might be introduced into a patient in the event of a leakage in the guidewire occlusion system 20.

A similar result could be achieved by manually attaching separate inflation syringes 114a, 114b, 114c and an evacuation syringe 112 directly to the sealing system 60 by way of a Luer lock or the like. While such an embodiment would not be as quick or convenient as the preferred embodiment, this alternative would eliminate the volume of gas required for the conduit 82 and within common housing 150, as well as the need for a valve arrangement 108.

Figure 15:
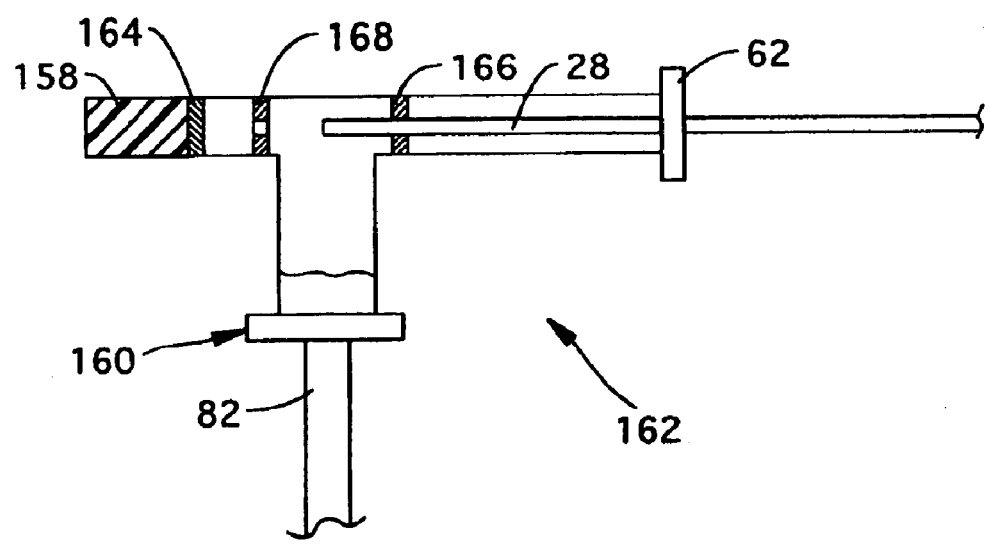
FIG. 15 is a cross-sectional view of an alternate embodiment of a sealing system showing one embodiment of a plugging mechanism.

In alternate embodiments, the sealing system could include means for selectively sealing involving techniques other than crimping to accomplish multiple airtight seals along the course of the extended sealable section 28. One alternate embodiment, as portrayed in FIG. 15, would involve the insertion of some form of sealant material 158 into the proximal end of the extended sealable section 28, such as wax, plastic, polymer or metal inserts or plugs. Conduit 82 is attached to a plugging mechanism 162 through the conduit aperture 160. In this embodiment, sealant material 158 is confined by sealant confinement layer 164 residing within plugging mechanism 162. Preferably for this embodiment, sealant material 158 is a wax or gel that is flowable at higher temperatures and might be melted during sterilization of the sealing system. Sealant confinement layer 164 is a foil layer or thin layer of non-meltable material capable of confining a flowable material during any sterilization process or exposure to higher temperature. The proximal end of extended sealable section 28 is inserted through first aperture 62 until it is past operational O-ring 166 or some other form of sealable/deformable material such as a silicone puncture seal or similar membrane seal. When it is desired to seal the extended sealable section 28, the extended sealable section 28 is further inserted past a sealant O-ring 168, then through sealant confinement layer 164, and finally into sealant material 158. Sealant material 158 is deposited in the proximal end of extended sealable section 28, thus preventing the guidewire assembly 22 from being evacuated. Extended sealable section 28 can then be slidably withdrawn through the sealant O-ring 168, through the operational O-ring 166, and through the first aperture 62, thereby effectively disengaging the guidewire assembly 22 from the plugging mechanism 162. The O-rings 166 and 168 serve as wiping structures to remove excess sealant material from the outside of the extended sealable section 28. Other alternate embodiments involve heating the extended sealable section 28 when it is formed of metal or polymer material so as to create a constriction, or applying electrical or magnetic energy to arc or weld material within the extended sealable section 28 to create a constriction. In one embodiment, the equivalent of a spot welder could be used in place of the crimping mechanism 66 to accomplish the same purpose of sealing, and then severing the extended sealable section 28. Alternative embodiments could use other sealing techniques to seal the guidewire assembly 22. These methods could include, but are not limited to, ones utilizing a heat source to melt the extended sealable section, ones using a heat source to apply a glue or gel, methods involving insertion of a plug material, methods using magnetics to manipulate a sealing material, or methods utilizing small occlusive devices.

Depending on the sealing method specified in an embodiment, different deflation techniques can be utilized. For the preferred embodiment, the extended sealable section 28 is of sufficient length to allow deflation through the shearing, breaking or opening of the extended sealable section 28 distal to the sealant material 158 located in the proximal end of the extended sealable section 28. By having sufficient length of the extended sealable section 28, the guidewire assembly 22 can be coupled to the gas inflation/evacuation system 80 (or 80a–80f) multiple times, allowing the occlusive balloon 32 to be inflated and deflated multiple times. Other embodiments will use methods of deflation including melting the sealant material 158, removing a plug of sealant material 158, and various other methods not requiring the extended sealable section 28 to be sheared.

Figure 16:
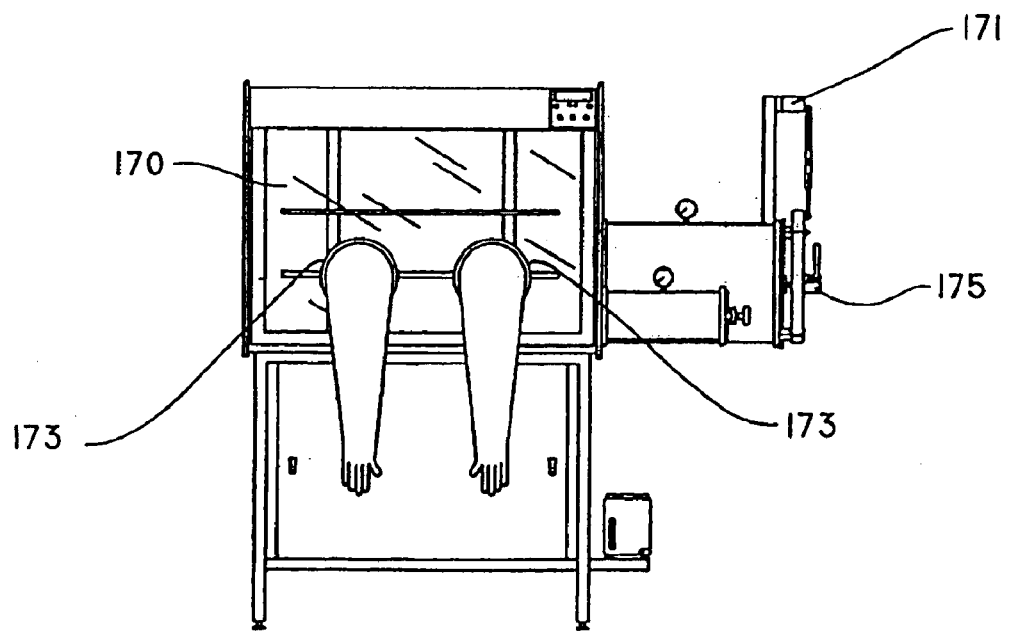
FIG. 16 is a schematic view of equipment including a sealed chamber for use in assembling and packaging the guidewire occlusion system.

In one embodiment, the guidewire occlusion system 20 is preferably pre-assembled and packaged in an environment consisting of an appropriate biocompatible gas. FIG. 16 shows equipment with which the guidewire occlusion system 20 is assembled and packaged. The guidewire occlusion system 20 is assembled and packaged in a sealed chamber 170. Sealed chamber 170 is equipped with a venting duct 171, sealed handling ports 173, and an atmosphere control system 175. The venting duct 171 and atmosphere control system 175 provide the overall system for maintaining a biocompatible gas atmosphere within the sealed chamber 170. Sensory readings within the sealed chamber 170 provide the atmosphere control system 175 with the data needed to adjust the biocompatible gas levels within the sealed chamber 170. Stored biocompatible gas is introduced into the sealed chamber 170 through the venting duct 171. Assembling and packaging of the guidewire occlusion system 20 and/or any of the pre-assembled components is achieved with the use of the sealed handling ports 173. The ports 173 are sterilized and sealed so that an assembler or packager positioned outside the sealed chamber 170 can access the contents of the chamber without introducing contamination through actual human contact or through the introduction of undesirable gases and airborne contaminants. These ports 173 could be constructed of flexible glove-like attachments, as shown, or they could be robotic devices operable within the sealed chamber 170 through controls external to the sealed chamber 170. The equipment could be two or more sealed chambers.

Figure 17:
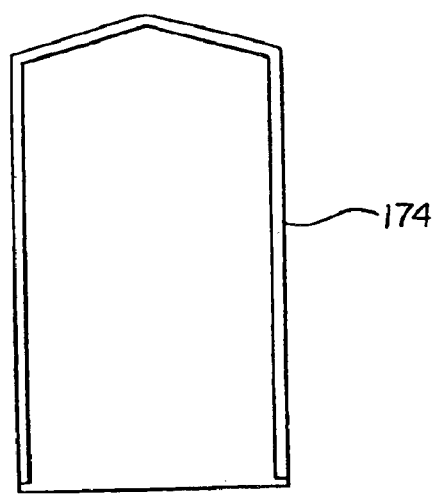
FIG. 17 is a side view of a biocompatible packaging.

After a guidewire assembly 22, a sealing system 60 (or 60a) and a gas inflation/evacuation system 80 (or 80a–80f) are placed in a sealed chamber 170, they are assembled to form the guidewire occlusion system 20 and placed into biocompatible packaging 174 (FIG. 17). Biocompatible packaging 174 is hermetically sealed so that the internal volume of both biocompatible packaging 174 and guidewire occlusion system 20 is composed solely of biocompatible gas. A preferred embodiment of the biocompatible packaging 174 is shown in FIG. 17. The biocompatible packaging 174 is preferably in the form of a foil pouch. This foil pouch is made from a medical packaging film with the following laminates: an 8.75 micron foil layer, an adhesive layer, a white polyethylene layer, and a 12 micron PET layer. The foil pouch has a preferred total thickness of approximately 3.6 millimeters, and a minimum bond strength of one pound. In addition, the preferred barrier properties of the film will be an oxygen transmission <0.01 cc/100 sq. in/24 hr. (73 degrees F., 0% RH) ASTM 3985, and moisture vapor transmission <0.01 gm H2O/100 sq. in/24 hr. (100 degrees F., 90% RH) ASTM F1249. It will be understood by those skilled in the art that this biocompatible foil pouch can be contained and/or attached within an outer packaging or container, such as a cardboard box, a plastic container, or the like. Such an outer packaging will facilitate shipping, labeling, storage, and handling of the biocompatible packaging 174 and its contents.

In practice, medical personnel gain access to the vessel lumen through which the guidewire assembly 22 will travel. The guidewire occlusion system 20 is removed from biocompatible packaging 174. Flexible tip 38 is inserted in the vessel lumen and is manipulated to a point beyond the vessel occlusion. Valve arrangement 84 (or 108) is adjusted to the evacuation position and evacuation syringe plunger 92 (or 100) is slidably withdrawn to remove any gas present in the guidewire assembly 22. Valve arrangement 84 (or 108) is then adjusted to the inflation position and inflation syringe plunger 94 (or 98, 98a, 98b, 98c) is slidably inserted causing occlusive balloon 32 to inflate.

Following inflation of occlusive balloon 32, handle 72 of the crimping mechanism 66 (or the handle of 66a) is depressed causing roller 76 and roller 78 to crimp and preferably sever the extended sealable section 28 of guidewire assembly 22. Severing of the extended sealable section 28 serves as an immediate verification of the creation of an effective seal. Sealing mechanism 68 (or 68a) can be released and guidewire assembly 22 can be completely removed from the sealing system 60 (or 60a) allowing the occlusive balloon 32 to remain inflated while occlusive substance treatment occurs. Following treatment, the extended sealable section 28 can be sheared or broken off, resulting in the deflation of the occlusive balloon 32. If occlusive treatment is complete, guidewire assembly 22 can be removed from the vessel lumen. If additional treatment is required, extended sealable section 28 can be reattached to sealing system 60 (or 60a) through first aperture 62. Sealing mechanism 68 (or 68a) can be retightened and the evacuation/inflation process can be repeated.

In a preferred embodiment of the present invention, the guidewire assembly 22 is utilized as the guidewire for an atherectomy or thrombectomy procedure of the type described in U.S. Pat. Nos. 5,370,609 or 5,496,267, the disclosures of both of which are hereby incorporated by reference. In each of these procedures, the guidewire assembly 22 is introduced into the patient, the occlusive balloon 32 is inflated, and then the atherectomy or thrombectomy catheter arrangement is slid over the proximal end 36 of the guidewire assembly 22 and advanced until it is proximate and proximal to the location of the occlusive balloon. The procedure is performed for a time period consistent with the desired maximum length for blockage of the particular vessel at which time the extended sealable section 28 of the guidewire assembly 22 may be severed to deflate the occlusive balloon 32, thereby reestablishing blood flow within the vessel. Depending upon the nature of the procedure, the catheter arrangement may be removed from the vessel or left in place. Preferably, an evacuation of any plaque material or other debris dislodged by the therapy is accomplished before deflation of the occlusive balloon 32. The occlusive balloon 32 is reinflated prior to reinitiation of the procedure.

The present invention may be embodied in other specific forms without departing from the essential attributes thereof; therefore, the illustrated embodiments should be considered in all respects as illustrative and not restrictive, reference being made to the appended claims rather than to the foregoing description to indicate the scope of the invention.

GAS INFLATION/EVACUATION SYSTEM AND SEALING SYSTEM FOR GUIDEWIRE ASSEMBLY HAVING OCCLUSIVE DEVICE
PARTS LIST

| | | | |
|---|---|---|---|
| 20 | guidewire occlusion system | 56 | protective polymer coating |
| 22 | guidewire assembly | 60 | sealing system |
| | | 60a | sealing system |
| 24 | proximal portion | 62 | first aperture |
| 26 | distal portion | 64 | second aperture |
| 28 | extended sealable section | 66 | crimping mechanism |
| 30 | main body portion | 66a | crimping mechanism |
| 32 | occlusive balloon | 68 | sealing mechanism |
| | | 68a | sealing mechanism |
| 34 | lumen | 70 | passageway |
| 35 | channel or hole | 72 | handle |
| 36 | proximal end | 74 | pivotable cam arrangement |
| 38 | flexible tip | | |
| 40 | distal end | 76 | roller |

-continued

GAS INFLATION/EVACUATION SYSTEM AND SEALING SYSTEM FOR GUIDEWIRE ASSEMBLY HAVING OCCLUSIVE DEVICE
PARTS LIST

| | | | |
|---|---|---|---|
| 42 | tapered portion | 78 | roller |
| 44 | laser weld | 80 | gas inflation/evacuation system |
| 46 | Ni-Ti or stainless steel sleeve | 80a–f | gas inflation/evacuation systems |
| 48 | laser weld | 82 | conduit |
| 50 | crimp | 84 | valve arrangement |
| 52 | proximal tip coil | 86 | evacuation syringe |
| 54 | distal tip coil | | |
| 88 | inflation syringe | 122 | conduit |
| 90 | pressure gauge | 126 | crimp body |
| 92 | evacuation syringe plunger | 128 | handle return |
| 94 | inflation syringe plunger | 132 | sealing body |
| 96 | assembly body | 138 | port |
| 98 | inflation syringe plunger | 139 | interconnect fitting |
| 98a–c | inflation syringe plungers | 140 | hose |
| 100 | evacuation syringe plunger | 141 | coupling |
| 102 | support structure | 142 | inflation manifold |
| 104 | fingergrip bore | 143 | tee connector |
| 106 | fingergrip | 144a–c | check valves |
| 108 | valve arrangement | 145 | coupling |
| 110a–c | interconnect fittings | 146 | connector |
| 111 | one-way check valve | 150 | common housing |
| 112 | evacuation syringe | 151 | top housing half |
| 113 | one-way check valve | 152 | structure |
| 114 | inflation syringe | 153 | bottom housing half |
| 114a–c | inflation syringes | 154 | fingergrip |
| 118 | assembly body | 156 | knob |
| 120 | knob | 158 | sealant material |
| 164 | sealant confinement layer | 160 | conduit aperture |
| 166 | operational O-ring | 162 | plugging mechanism |
| 168 | sealant O-ring | | |
| 170 | sealed chamber | | |
| 171 | venting duct | | |
| 173 | sealed handling port | | |
| 174 | biocompatible packaging | | |
| 175 | atmosphere control system | | |

What is claimed is:

1. A gas inflation/evacuation system and sealing system removably connectible to a proximal portion of a guidewire assembly which has an occlusive balloon at a distal portion thereof, comprising:

means for evacuating the guidewire assembly;

means for introducing a biocompatible gas into the guidewire assembly to inflate the occlusive balloon at the distal portion of the guidewire assembly a plurality of times; and, means for selectively sealing the guidewire assembly by forming successive permanent airtight seals at separate locations along the proximal portion of the guidewire assembly to retain the biocompatible gas in the occlusive balloon a plurality of times, the means for selectively sealing including a mechanism selected from the group of mechanisms consisting of a crimping mechanism and a plugging mechanism.

2. The gas inflation/evacuation system and sealing system of claim 1, wherein the means for evacuating, the means for introducing a biocompatible gas, and the means for selectively sealing constitute a handheld apparatus.

3. The gas inflation/evacuation system and sealing system of claim 2, wherein the means for selectively sealing includes a first aperture into which the proximal portion of the guidewire assembly is selectively insertable, a second aperture to which the means for evacuating and the means for introducing a biocompatible gas are operably connected, and an airtight passageway connecting the first aperture and the second aperture.

4. The gas inflation/evacuation system and sealing system of claim 1, wherein the mechanism is a crimping mechanism.

5. The gas inflation/evacuation system and sealing system of claim 4, wherein the crimping mechanism comprises:
a first roller and a second roller proximately spaced from the first roller for traversal of the proximal portion of the guidewire assembly, the first roller being connected to a handle with a pivotable cam arrangement such that force on the handle causes the first roller to proportionately approach the second roller, a first threshold force on the handle causing sealing of the proximal portion of the guidewire assembly and a second threshold force on the handle causing severing of the proximal portion of the guidewire assembly.

6. The gas inflation/evacuation system and sealing system of claim 5, wherein the handle is spring biased for an automatic return to an open starting position upon the cessation of a force.

7. The gas inflation/evacuation system and sealing system of claim 1, wherein the mechanism is a plugging mechanism that selectively inserts a plug of material into the proximal portion of the guidewire assembly while maintaining an airtight seal between the guidewire assembly and the means for evacuating and the means for introducing a biocompatible gas.

8. The gas inflation/evacuation system and sealing system of claim 1, wherein the means for evacuating, the means for introducing a biocompatible gas, and the means for selectively sealing are contained in a sterile packaging filled with a biocompatible gas and wherein all gas within the sterile packaging is selected from the group consisting of carbon dioxide, oxygen, and nitrous oxide.

9. A gas inflation/evacuation system and sealing system removably connectible to a proximal portion of a guidewire assembly which has an occlusive balloon at a distal portion thereof, comprising:
a first syringe that selectively evacuates the guidewire assembly;
a second syringe that selectively introduces a biocompatible gas into the guidewire assembly to inflate the occlusive balloon at the distal portion of the guidewire assembly a plurality of times;
a sealing assembly removably connectible to the proximal portion of the guidewire assembly, the sealing assembly including a mechanism that selectively seals the proximal portion of the guidewire assembly at one of a plurality of separate locations to form one of a plurality of successive permanent airtight seals of the guidewire assembly; and,
a valve arrangement that selectively opens and closes communication between the sealing assembly and the first syringe and between the sealing assembly and the second syringe.

10. The gas inflation/evacuation system and sealing system of claim 9, wherein the first syringe, the second syringe, and the sealing assembly form a handheld apparatus and wherein the sealing assembly includes a first aperture into which the proximal portion of the guidewire assembly is selectively insertable, a second aperture to which the first and second syringes are operably connected, and an airtight passageway connecting the first aperture and the second aperture.

11. The gas inflation/evacuation system and sealing system of claim 9, wherein the mechanism is a crimping mechanism which permanently deforms and crimps the proximal portion of the guidewire assembly.

12. The gas inflation/evacuation system and sealing system of claim 11, wherein the crimping mechanism comprises:
a first roller and a second roller proximately spaced from the first roller for traversal of the proximal portion of the guidewire assembly, the first roller being connected to a handle with a pivotable cam arrangement such that force on the handle causes the first roller to proportionately approach the second roller, a first threshold force on the handle causing sealing of the proximal portion of the guidewire assembly and a second threshold force on the handle causing severing of the proximal portion of the guidewire assembly.

13. The gas inflation/evacuation system and sealing system of claim 12, wherein the handle is spring biased for an automatic return to an open starting position upon cessation of a force.

14. The gas inflation/evacuation system and sealing system of claim 9, wherein the mechanism is a plugging mechanism that selectively inserts a plug of material into the proximal portion of the guidewire assembly while maintaining an airtight seal between the guidewire assembly and the first and second syringes.

15. The gas inflation/evacuation system and sealing system of claim 9, wherein the first and second syringes, the sealing assembly, and the valve arrangement are contained in a sterile packaging filled with a biocompatible gas and wherein all gas within the sterile packaging is selected from the group consisting of carbon dioxide, oxygen, and nitrous oxide.

16. A gas inflation/evacuation system and sealing system selectively operably connectable to and removable from a proximal portion of a guidewire assembly which has an occlusive balloon at a distal portion thereof, comprising:
a handheld unit including a crimping mechanism having a first aperture and a sealing mechanism having a second aperture, there being a passageway extending from the first aperture to the second aperture for receiving the proximal portion of the guidewire assembly;
a first syringe system that selectively evacuates the guidewire assembly;
a second syringe system containing a volume of a biocompatible gas sufficient to inflate the occlusive balloon at the distal portion of the guidewire assembly a plurality of times; and,
conduits operably connecting the first syringe system and the second syringe system to the second aperture of the handheld unit, the conduits including a valve arrangement that selectively connects only one of the first syringe system and the second syringe system to the second aperture at a time.

17. The gas inflation/evacuation system and sealing system of claim 16, wherein the second syringe system includes a plurality of individual syringes, each individual syringe containing a sufficient volume of biocompatible gas to inflate the occlusive balloon one time.

18. The gas inflation/evacuation system and sealing system of claim 16, wherein the crimping mechanism comprises:

a first roller and a second roller proximately spaced from the first roller for traversal of the proximal portion of the guidewire assembly, the first roller being connected to a handle with a pivotable cam arrangement such that force on the handle causes the first roller to proportionately approach the second roller, a first threshold force on the handle causing sealing of the proximal portion of the guidewire assembly and a second threshold force on the handle causing severing of the proximal portion of the guidewire assembly.

19. The gas inflation/evacuation system and sealing system of claim 18, wherein the handle is spring biased for an automatic return to an open starting position upon cessation of a force.

20. A gas inflation/evacuation system and sealing system removably connectible to a proximal portion of a guidewire assembly which has an occlusive balloon at a distal portion thereof, comprising:

a handheld unit including a crimping mechanism having a first aperture and a sealing mechanism having a second aperture, there being a passageway extending from the first aperture to the second aperture for receiving the proximal portion of the guidewire assembly;

an evacuating syringe that selectively evacuates the guidewire assembly; and, a plurality of inflation syringes, each inflation syringe containing a volume of a biocompatible gas sufficient to inflate the occlusive balloon at the distal portion of the guidewire assembly a single time.

21. The gas inflation/evacuation system and sealing system of claim 20, further comprising:

conduits operably connecting the evacuation syringe and the plurality of inflation syringes to the second aperture of the handheld unit, the conduits including a valve arrangement that selectively connects only the evacuation syringe or the plurality of inflation syringes to the second aperture at one time.

22. The gas inflation/evacuation system and sealing system of claim 20, wherein the handheld unit, the evacuation syringe, and the plurality of inflation syringes are contained in a sterile packaging filled with a biocompatible gas and wherein all gas within the sterile packaging is selected from the group consisting of carbon dioxide, oxygen, and nitrous oxide.

23. A gas inflation/evacuation system and sealing system removably connectible to a proximal portion of a guidewire assembly which has an occlusive balloon at a distal portion thereof, comprising:

a first syringe system that selectively evacuates the guidewire assembly;

a second syringe system that selectively introduces a biocompatible gas into the guidewire assembly to inflate the occlusive balloon at the distal portion of the guidewire assembly a plurality of times; and a plugging mechanism removably connectible to the proximal portion of the guidewire assembly that selectively seals the proximal portion of the guidewire assembly at one of a plurality of separate locations to form one of a plurality of successive permanent airtight seals of the guidewire assembly, including:

a first aperture and a second aperture in fluid communication, the first aperture being capable of receiving therethrough the proximal portion of the guidewire assembly, and the second aperture being removably attachable to a conduit;

an operational O-ring in coaxial alignment with the first aperture for operational engagement of the proximal portion of the guidewire assembly at a location proximal of the first aperture;

a sealant O-ring in coaxial alignment with the first aperture and proximally spaced from the operational O-ring such that further insertion of the proximal portion of the guidewire assembly through the first aperture and past the operational O-ring will bring the proximal portion of the guidewire assembly into engagement with the sealant O-ring; and, a sealant confinement layer for receiving the proximal portion of the guidewire assembly some distance past the sealant O-ring, the sealant confinement layer confining sealant material such that insertion of the proximal portion of the guidewire assembly through the sealant confinement layer and into the sealant material forces the sealant material into the proximal portion of the guidewire assembly.

24. The gas inflation/evacuation system and sealing system of claim 23, wherein the sealant material is selected from the group consisting of wax, plastic, polymer, and metal.

25. The gas inflation/evacuation system and sealing system of claim 1, wherein the means for evacuating comprises at least one syringe and the means for introducing a biocompatible gas comprises at least one syringe.

26. The gas inflation/evacuation system and sealing system of claim 1, further comprising means for severing the proximal portion of the guidewire assembly distal to each successive permanent airtight seal to reopen the proximal portion of the guidewire assembly to release the biocompatible gas from the occlusive balloon.

27. The gas inflation/evacuation system and sealing system of claim 9, further comprising a severing mechanism for removing the portion of the proximal portion of guidewire assembly containing a permanent airtight seal.

* * * * *